United States Patent [19]

Ishida

[11] E Patent Number: Re. 32,637

[45] Reissued Date of Patent: Apr. 5, 1988

[54] PHYSIOLOGICALLY ACTIVE PEPTIDE

[75] Inventor: Torao Ishida, Nagareyama, Japan

[73] Assignee: Asahi Kasei Kogyo Kabushiki Kaisha, Osaka, Japan

[21] Appl. No.: 881,759

[22] Filed: Jul. 3, 1986

Related U.S. Patent Documents

Reissue of:

[64] Patent No.: 4,457,867
Issued: Jul. 3, 1984
Appl. No.: 450,721
Filed: Dec. 17, 1982

[30] Foreign Application Priority Data

Dec. 24, 1981 [JP] Japan ..... 56-213763

[51] Int. Cl.[4] ..... C07K 13/00

[52] U.S. Cl. ..... 530/350; 530/324; 530/328; 530/329; 530/330; 530/351

[58] Field of Search ..... 530/351, 350, 330, 329, 530/328, 324

[56] References Cited

FOREIGN PATENT DOCUMENTS 2040292 8/1980 United Kingdom .
2063882 6/1981 United Kingdom .
2071108 9/1981 United Kingdom .

OTHER PUBLICATIONS

Nucleic Acids Research, vol. 10, No. 8, (Apr. 8, 1982), 2487–2501.
Interferon, 4, 1982, Academic Press, pp. 130–154.
Nature, vol. 287, (1980), 411–414.
Chem. Abstr., vol. 96, (1982), 120770.
Proc. Natl. Acad. Sci., 78, (1981), 3469–3472.
Biochem. and Biophys. Res. Commun., (1981), 865–871, vol. 100, No. 2.
Eur. J. Immunol., (1980), 10, 877–883.
Proc. Natl. Acad. Sci., 78, No. 3, 1601–1605.
Nature, 292, (1981), 842–844.
Twigg et al. *Nature*, 283, 216–217 (1980).
Edge et al., *Nature*, 292, 756–762 (1981).
T. Taniguchi, et al., "The Nucleotide Sequence of Human Fibroblast Interferon cDNA", Gene, 10, 11–15 (1980).
D. V. Goeddel, "The Structure of Eight Distinct Cloned Human Leukocyte Interferon cDNAs", Nature, 290, 20 (1981).
Y. K. Yip, et al., "Partial Purification and Characterization of Human γ (immune) Interferon", Proc. Natl. Acad. Sci. USA, 78, 1601–1605 (1981).
Abstract of D. V. Goeddel–"Synthesis of Human Interferons in *E. coli* and Yeast", The Second Annual International Congress for Interferon Research held in San Francisco, U.S.A. on Oct. 21–23, 1981.

*Primary Examiner*—Delbert R. Phillips
*Attorney, Agent, or Firm*—Pennie & Edmonds

[57] ABSTRACT

A novel physiologically active peptide represented by the following formula:

$$BCysX_1CysX_2CysX_3$$

(wherein B stands for a hydrogen atom or a methionyl group, Cys a cysteine residue, $X_1$ [5 to 9 amino acid residues] *an isoleucylvalylleucylglycylserylleucylglycine residue*, $X_2$ [one amino acid residue] *a tyrosine residue*, and $X_3$ [138 to 148 amino acid residues] *a specific sequence of 143 amino acid residues as defined herein*), which is excellent in physiological activities such as antiviral action, cell proliferation inhibitive action and NK (natural killer) cell activity enhancing action, *and a short sequence peptide represented by the above-mentioned* $X_3$.

2 Claims, No Drawings

PHYSIOLOGICALLY ACTIVE PEPTIDE

Matter enclosed in heavy brackets [ ] appears in the original patent but forms no part of this reissue specification; matter printed in italics indicates the additions made by reissue.

This invention relates to a novel physiologically active peptide which is excellent in physiological activities such as antiviral action, cell proliferation inhibitive action and NK (natural killer) cell activity enhancing action. More particularly, the present invention is concerned with a novel physiologically active peptide represented by the following formula (I):

$$BCysX_1CysX_2CysX_3 \quad (I)$$

where B stands for a hydrogen atom or a methionyl group, Cys a cysteine residue, $X_1$ [5 to 9 amino acid residues] *an isoleucylvalleucylglycylserylleucylglyceine residue*, $X_2$ [one amino acid residue] *a tyrosine residue*, and $X_3$ [138 to 148 amino acid residues] *a specific sequence of 143 amino acid residues as defined herein. The present invention also relates to a peptide comprising a specific amino acid sequence of 143 amino acid residues which peptide has one utility as an intermediate for the production of the physiologically active peptide.*

Heretofore, antimetabolites, alkylating agents, antibiotics and the like have been used as antiviral agents or cell proliferation inhibitors, but they are disadvantageously high in toxicity. Accordingly, the development of an antiviral agent or cell proliferation inhibitor having a low toxicity has been strongly desired in the art.

Recently, studies of α interferon (hereinafter referred to as "[IFN-α] *IFN-β*") and β interferon (hereinafter referred to as "IFN-β") have made progress since they are effective as [low toxicily] *low toxicity* antiviral agents. But, the cell proliferation inhibitive effect of IFN-α and IFN-β is not satisfactory. On the other hand, the studies of γ interferon (hereinafter referred to as "IFN-γ") has not made progress as compared with the studies of IFN-α and IFN-β.

However, in the Second Annual International Congress for Interferon Research held on October, 1981 at San Francisco in U.S.A., although IFN-γ has not been isolated, David V. Goeddel (Genentech, Inc., California, U.S.A.) reported an amino acid sequence of each of pro-IFN-γ, IFN-γ and IFN-γ-like peptide which was estimated from a deoxyribonucleotide sequence of a complementary DNA (hereinafter frequently referred to as "cDNA") of IFN-γ messenger RNA (hereinafter frequently referred to as "mRNA"). The amino acid sequence of each of pro-IFN-γ, IFN-γ and IFN-γ-like peptide will be described later. In the congress mentioned above, it was also reported that the culture of the cell having the gene encoding IFN-like peptide has an antiviral activity whereas the culture of the cell having the gene encoding pro-IFN-γ does not. Whilst, the preparation of the culture of the cell encoding IFN-γ has not yet been successfully made.

In view of the current situation as mentioned above, the present inventor has made extensive and intensive studies with a view to developing a physiologically active agent which not only has an excellent antiviral activity but also exhibits an excellent cell proliferation inhibitive action and NK cell activity enhancing action. As a result, the present inventor has suprisingly found that a peptide represented by the formula(I) as mentioned above not only is very excellent in all of the above-mentioned physiological activities, but also exhibits a low toxicity. The present invention has been made based on such a novel finding.

Therefore, it is an object of the present invention to provide a novel physiologically active agent which not only is excellent in antiviral activity but also exhibits an excellent cell proliferation inhibitive action and NK cell activity enhancing action.

Other objects and advantages of the present invention will become apparent from the detailed description to follow taken in conjunction with the appended claims.

In accordance with the present invention, there is provided a novel physiologically active peptide represented by the following formula (I):

$$BCysX_1CysX_2CysX_3 \quad (I)$$

wherein B stands for a hydrogen atom *or a methionyl group, Cys a cysteine residue, $X_1$ 5 to 9 amino acid residues, $X_2$ one amino acid residue, and $X_3$ 138 to 148 amino acid residues* or a methionyl group, Cys a cysteine residue, $X_1$ [5 to 9 amino acid residues] *an isoleucylvalylleucylglycylserylleucylglycine residue*, $X_2$ [one amino acid residue] *a tyrosine residue*, and $X_3$ [138 to 148 amino acid residues.] *a residue of an amino acid sequence represented by the following formula (II)*:

*Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln*

*wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Met a methionine residue.*

*Further, according to the present invention, there is provided a peptide comprising an amino acid sequence represented by the formula (II) mentioned above.*

The physiologically active peptide of the present invention is similar in amino acid sequence to pro-IFN-γ, IFN-γand IFN-γ-like peptide but is remarkably different in physiological activity from them as will be described below.

The amino acid sequence of pro-IFN-γ corresponds to the amino acid sequence which is formed by attachment of additional 12 amino acid residues to the N-terminus of a certain peptide belonging to the novel physiologically active peptide of the present invention represented by the above formula (I) wherein B stands for a hydrogen atom. However, while the novel physiologically active peptide of the present invention is excellent in antiviral action, cell proliferation inhibitive action and NK cell activity enhancing action, pro-IFN-γ exhibits no such actions.

The amino acid sequence of IFN-γ-like peptide corresponds to the amino acid sequence which is formed by the deletion of the peptide residue represented by $CysX_1$ (wherein Cys and $X_1$ are as defined above) from a certain peptide belonging to the novel physiologically active peptide of the present invention represented by the above formula (I) wherein B stands for a methionyl group. The amino acid sequence of IFN-γ corresponds to the amino acid sequence which is formed by the deletion of the peptide residue represented by $CysX_1$ (wherein Cys and $X_1$ are as defined above) from a certain peptide belonging to the novel physiologically active peptide of the present invention represented by the above formula (I) wherein B stands for a hydrogen atom. However, IFN-γ-like peptide and IFN-γ are poor not only in antiviral activity but also in cell proliferation inhibitive action and NK cell activity enhancing action as compared with the physiologically active peptide of the present invention.

As is apparent from the foregoing, the peptide of the present invention is a novel physiologically active peptide which is similar in amino acid sequence to the known substances pro-IFN-γ, IFN-γ and IFN-γ-like peptide but is completely different in physiological activity from them.

The reason for the great difference in physiological activity between the physiologically active peptide of the present invention and pro-IFN-γ, IFN-γ and IFN-γ-like peptide as mentioned above is not yet fully elucidated. But, one of the reasons for this is believed to be as follows. The three cysteine residues in the peptide residues represented by $CysX_1CysX_2Cys$ (wherein Cys, $X_1$ and $X_2$ are as defined above) of the peptide of the present invention represented by the formula(I) above contribute to the excellent physiological activity of the peptide of the present invention. It is believed that by the deletion of the peptide residue represented by $CysX_1$ (wherein Cys and $X_1$ are as defined above) from $CysX_1CysX_2Cys$ (wherein Cys $X_1$ and $X_2$ are as defined above), the physiological activity is lowered and that by the addition of 12 amino acid residues to a N-terminus of $CysX_1CysX_2Cys$ (wherein Cys, $X_1$ and $X_2$ are as defined above), the physiological activity is lost.

As mentioned above, the novel physiologically active peptide of the present invention is represented by the following formula(I):

$$BCysX_1CysX_2CysX_3 \quad (I)$$

wherein B, Cys, $X_1$, $X_2$ and $X_3$ are as defined above. [In the peptide of the present invention represented by the above formula(I), a preferable peptide is one in which, in the above formula(I), $X_1$ is 7 amino acid residues and $X_3$ is 143 amino acid residues. A more preferable peptide is one in which $X_1$ is an isoleucylvalylleucylglycylserylleucylglycine residue and $X_2$ is a tyrosine residue. The most preferable peptide is one in which $X_1$ is an isoleucylvalylleucylglycylserylleucylglycine residue, $X_2$ is a tyrosine residue and $X_3$ is a residue represented by the formula(II):

Gln Asp Pro Tyr Val Lys Glu Ala Glu Asn Leu Lys
Lys Tyr Phe Asn Ala Gly His Ser Asp Val Ala
Asp Asn Gly Thr Leu Phe Leu Gly Ile Leu Lys
Asn Trp Lys Glu Glu Ser Asp Arg Lys Ile Met
Gln Ser Gln Ile Val Ser Phe Tyr Phe Lys Leu Phe
Lys Asn Phe Lys Asp Asp Gln Ser Ile Gln Lys Ser
Val Glu Thr Ile Lys Glu Asp Met Asn Val Lys
Phe Phe Asn Ser Asn Lys Lys Lys Arg Asp Asp
Phe Glu Lys Leu Thr Asn Tyr Ser Val Thr Asp
Leu Asn Val Gln Arg Lys Ala Ile His Glu Leu Ile
Gln Val Met Ala Glu Leu Ser Pro Ala Ala Lys
Thr Gly Lys Arg Lys Arg Ser Gln Met Leu Phe
Arg Gly Arg Arg Ala Ser Gln wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn as asparagine residue, Leu a leucine residue, Phe a phenylalanine residue, Gly a glycerine residue, His a histidine residue, Ser a serine residue, Thr a threonine residue, Ile an isoleucine residue, Trp a tryptophan residue, Arg an arginine residue, and Met a methionine residue.]

On the other hand, the amino acid sequence of pro-IFN-γ, IFN-γ and IFN-γ-like peptide reported by David V. Goeddel in the Second Annual International Congress for Interferon Research as mentioned above is represented by the following formula(III):

J Cys Tyr Cys Gln Asp Pro Tyr Val Lys Glu Ala
Glu Asn Leu Lys Lys Tyr Phe Asn Ala Gly His
Ser Asp Val Ala Asp Asn Gly Thr Leu Phe Leu
Gly Ile Leu Lys Asn Trp Lys Glu Glu Ser Asp
Arg Lys Ile Met Gln Ser Gln Ile Val Ser Phe Tyr
Phe Lys Leu Phe Lys Asn Phe Lys Asp Asp Gln
Ser Ile Gln Lys Ser Val Glu Thr Ile Lys Glu Asp
Met Asn Val Lys Phe Phe Asn Ser Asn Lys Lys
Lys Arg Asp Asp Phe Glu Lys Leu Thr Asn Tyr
Ser Val Thr Asp Leu Asn Val Gln Arg Lys Ala Ile
His Glu Leu Ile Gln Val Met Ala Glu Leu Ser Pro
Ala Ala Lys Thr Gly Lys Arg Lys Arg Ser Gln
Met Leu Phe Arg Gly Arg Arg Ala Ser Gln wherein Cys, Tyr,Gln,Asp,Pro,Val, Lys,Glu,Ala,Asn, Leu,Phe,Gly,His,Ser,Ile,Trp,Arg,Met and Thr are as defined above; and J stand for Met Lys Tyr Thr Ser Tyr Ile Leu Ala Phe Gln Leu Cys Ile Val Leu Gly Ser Leu Gly (wherein Met, Lys, Tyr, Thr, Ser, Ile, Leu, Ala, Phe, Gln, Cys and Val are as defined above) in the case of pro-IFN-γ, a hydrogen atom in the case of IFN-γ and a methionyl group in the case of IFN-γ-like peptide.

The novel physiologically active peptide of the present invention may be produced by conventionally known methods as disclosed in Nobuo Izumiya et al, "Synthetic Chemistry Series-Syntheses of Peptides" published by Maruzen K.K., Japan, 1975; "Experimental Biochemistry/Chemistry of Proteins I–IV" edited by the Japanese Biochemical Society and published by Tokyo Kagaku Dozin, Japan, 1977; "Genetic Engineering", Protein, Nucleic Acid and Enzyme, Vol. 26, No. 4 published by Kyoritsu Shuppan K.K., Japan, 1981; and "Advances in Interferon Researches", Protein, Nucleic Acid and Enzyme, separate Vol. No. 25 published by Kyoritsu Shuppan K.K., Japan, 1981. The processes by which the novel physiologically active peptide of the present invention may be produced can be divided into the following three groups:

(1) a process in which a peptide is prepared by chemical synthesis;

(2) a process in which a gene prepared by chemical synthesis is inserted into a host and a peptide is produced by the host; and (3) a process in which a gene obtained biotechnically is inserted into a host and a peptide is produced by the host.

As one mode of the first process as mentioned above, the solid phase method will be specifically described below. The carboxyl group in an amino acid having an α-amino protecting group is bonded to a substrate, for example, a polystyrene resin crosslinked with divinylbenzene. Then, the α-amino protecting group is selectively removed. The resulting free amino group is reacted with a second amino acid having an α-amino protecting group. The removal of the α-amino protecting group and the introduction of the amino acid having an α-amino protecting group are repeated until the intended peptide chain is obtained. Then the covalent bond between the carboxyl group of the C-terminal amino acid of the peptide and the resin is cleaved. Some agents employed for cleaving the covalent bond can effect the removal of the α-amino protecting group or side chain protecting group and the cleavage of the covalent bond simultaneously.

The solid phase method as described above is advantageous over the so-called liquid phase method in that the production of the peptide can be simply carried out because all the reactions required can be carried out in a single vessel; and that the intended peptide can be produced not only in a short period of time but also in high yield because the obtained product is insoluble in a solvent used for the reaction and, therefore, the excess amount of reagent used and by-products can be removed by filtration.

As the substrate to be used in the first process, a styrene polymer which is crosslinked with divinylbenzene (crosslinking degree:2%) and has a size of 200 to 400 mesh is generally preferred. Prior to the reaction of the resin with the amino acid, a functional group is introduced into the resin to impart the reactivity to the resin. In general, to introduce a functional group into the resin, there may be employed a method in which the aromatic ring of the styrene unit is reacted with chloromethyl methyl ether using $SnCl_2$ as a catalyst by a Friedel-Crafts reaction to chloromethylate the aromatic ring of the styrene unit.

As the α-amino protecting group used in the first process, preferred is a group which is stable in coupling reaction and can be easily removed without any adverse effect on the side chain protecting group and the peptide chain. As such a preferable α-amino protecting group, a tertiary butoxy carbonyl (hereinafter frequently referred to as "Boc") group may be mentioned. The Boc group is easily removed from the peptide chain with an 1N HCl/acetic acid mixture, 4N HCl/dioxane mixture or 50% [w/v)] *w/v* TfaOH (tetrafluoro acetic acid)/$CH_2Cl_2$ mixture.

As the side chain protecting group, preferred is a group which is stable in coupling reaction as well as in removal of the γ-amino protecting group and can be easily removed in the final step of the synthesis of the peptide. As such a preferable side chain protecting group, there may be mentioned a $NO_2$ or tosyl group for arginine; a benzyl (hereinafter frequently referred to as "Bzl") group for aspartic acid; a benzyl or o-methylbenzyl (hereinafter frequently referred to as "OBzl") group for cysteine and glutamic acid; a benzyl, benzyloxycarbonyl (hereinafter frequently referred to as "Z"), or Boc group for histidine; a Z, tosyl or diisopropylmethyloxycarbonyl (Dipmoc) group for lysine; a sulfoxide group for methionine; and a benzyl group for serine, threonine and tyrosine.

The second process as mentioned above will be specifically described below. Genetic codes for the respective amino acid residues of the intended peptide are selected from the amino acid sequence of the intended peptide. A hybrid double stranded DNA fragment comprising a strand encoding the physiologically active peptide of the present invention is synthesized by chemical synthesis based on the genetic code. The synthesized DNA fragment is inserted into a replicable expression vehicle as a vector. The DNA fragment inserted into the vector is then inserted into unicellular organisms.

By the insertion of the vector inserted DNA fragment into unicellular organisms, the unicellular organisms are transformed to form transformants. The resulting transformants are customarily isolated from parent unicellular organisms by means of a phenotypical trait imparted by the DNA fragment. The isolated transformants are cultured to produce the peptide. In this process, peptides in which B in the formula(I) of the peptide of the present invention is a methionyl group (hereinafter frequently referred to as "MC peptide") are produced. When the MC peptides are partially hydrolyzed using an aminopeptidase, peptides in which B in the formula(I) of the peptide of the present invention is a hydrogen atom (hereinafter frequently referred to as "HC peptide") can be obtained.

As unicellular organisms or hosts which are employed in this process, there may be mentioned microorganisms, mammalian cells, plant cells and the like. Among them, microorganisms and mammalian cells are preferably employed. As the preferable microorganisms, there may be mentioned yeast and bacteria such as Escherichia coli, Bacillus subtilis, Actinomyces, Bacillus stearothermophilus.

Replicable expression vehicles or vectors used in this process should be those which are capable of infecting the above-mentioned hosts therewith. As such vectors, there may be mentioned plasmids, phages, viruses and the like. The above-mentioned vectors and hosts may also be employed for the production of the peptide from a gene obtained biologically. The following genetic code for each of amino acid residues is used for the synthesis of a gene for the peptide of the present invention in which A stands for a deoxyadenylic acid residue, G a deoxyguanylic acid residue, C a deoxycytidylic acid residue and T a thymidylic acid residue and in which the left end of the genetic code and the right end of the genetic code represent 5'-hydroxyl group side and 3'-hydroxyl group side, respectively: TTT or TTC for phenylalanine; TTA, TTG, CTT, CTC, CTA or CTG for leucine; ATT, ATC or ATA for isoleucine; ATG for methionine; GTT, GTC, GTA or GTG for valine; TCT, TCC, TCA, TCG, AGT or AGC for serine; CCT, CCC, CCA or CCG for proline; ACT, ACC, ACA or ACG for threonine; GCT, GCC, GCA or GCG for alanine; TAT or TAC for tyrosine; CAT or CAC for histidine; CAA or CAG for glutamine, AAT or AAC for asparagine; AAA or AAG for lysine; GAT or GAC for aspartic acid; GAA or GAG for glutamic acid; TGT or TGC for cysteine; TGG for tryptophan; CGT, CGC, CGA, CGG, AGA or AGG for arginine; and GGT, GGC, GGA or GGG for glycine. In addition, ATG is used for initiation of the peptide synthesis as well as for methionine and TAA, TAG and TGA are used for termination of the peptide synthesis. In the gene, the above-mentioned four deoxyribonucleoside bases are linked by phosphodestic bonds between their respective 3' and 5' positions. Therefore, the gene for the peptide can be synthesized using a protecting group and a condensing agent. As preferable protecting groups, there can be mentioned those which can, protect selectively a predetermined site of the deoxyribonucleotide, which are stable during the reaction and which are easily removed without cleaving the internucleotide bond. Further, the intermediates should be separated and purified with ease. For those reasons, the following triester method is preferred to synthesize a gene for the peptide. Trimer blocks corresponding to the amino acid code and if necessary dimer [clock] *blocks* are first synthesized. The blocks are then condensed to form an oligomer comprising a chain of about 12 to 23 nucleotides. It is preferred that the condensation be carried out by the solid phase method in which a substrate such as polymer is used. The resulting oligomer is elongated using a DNA ligase to form a gene for the intended peptide.

As the amino-protecting group of the above-mentioned deoxyribonucleosides, a benzoyl group is desirable for deoxycytidine and deoxyadenosine, and an isobutyl group is desirable for deoxyguanosine. As the hydroxyl-protecting group, a trityl group, an acyl group, a silyl group and groups derived therefrom may be used. Among them, the groups derived from a trityl group are preferably employed. As the condensation agent, a strong condensation agent such as 2,4,6-triisopropylbenzenesulfonyl tetrazolide (hereinafter frequently referred to as "TPSTe") is desirable. The protecting groups of oligonucleotides obtained by condensation of deoxyribonucleotides may be removed by the following method. The amino-protecting groups and 3'-hydroxyl-protecting groups such as groups derived from an acyl group are removed with aqueous ammonia and the 5'-hydroxyl-protecting groups, e.g., groups derived from a trityl group are then removed with 80% by volume acetic acid.

The advantage of preparing a gene by chemical synthesis is that the production of the peptide can be increased by using a genetic code which abundantly exists in a host used for the production of the peptide.

The method of inserting the synthesized gene into a vector; the method of inserting the gene-inserted vector into a host in order to transform the host; and the method of culturing the transformed host to produce the novel physiologically active peptide of the present invention are the same as those using a natural gene as described below.

The third process consists in obtaining biotechnically a gene, i.e. a hybrid double stranded DNA fragment comprising a strand encoding the peptide of the present invention; inserting the DNA fragment into a replicable expression vehicle as a vector; transforming unicellular organisms with the DNA fragment inserted into the vehicle to form transformants; isolating said transformants from parent unicellular organisms by means of a phenotypical trait imparted by said DNA fragment; and culturing the transformants to produce the physiologically active peptide of the present invention.

Specific kinds of peptides may be produced by the above-mentioned method. Illustratively stated, by this method, there may be produced novel physiologically active peptides of the present invention having a general formula(I) as described before wherein $X_1$ stands for an isoleucylvalylleucylglycylserylleucylglycine residue, $X_2$ stands for a tyrosine residue and $X_3$ stands for a specific peptide residue represented by the formula(II) as mentioned before. Further, by this method, there may occasionally be produced peptides of the present invention having a general formula(I) as described before wherein $X_1$ and $X_2$ are as defined immediately above and $X_3$ stands for a residue represented by the above-mentioned formula(II) with [its] some *of its* amino acid residues converted to other kinds of amino acid residues, with some of *its* amino acid residues deleted therefrom or with some other kinds of amino acid residues attached thereto. One mode of the third process will be specifically described below. The formation of mRNA is induced by stimulating human peripheral blood lymphocytes with a mitogen, and then the lymphocytes are denatured. Thereafter, RNA containing mRNA is separated from the denatured lymphocytes by centrifugation. The mRNA is then separated from the obtained RNA containing mRNA using an oligo(dT-)cellulose column. Using the obtained mRNA as a template, in the presence of oligo(deoxyribosylthymine monophosphate) [hereinafter frequently referred to as "oligo(dT)], deoxyadenosine triphosphate [hereinafter frequently referred to as "dATP"], deoxycytosine triphosphate [hereinafter frequently referred to as "dCTP"], [deoxguanosine] *deoxyguanosine* triphosphate [hereinafter frequently referred to as "dGTP"] and deoxyribosylthymine triphosphate [hereinafter frequently referred to as "dTTP"], a double strand of mRNA and complimentary DNA (hereinafter frequently referred to as "cDNA") is formed by a reverse transcriptase. From the thus obtained mRNA.cDNA double strand, mRNA is removed by alkali treatment or heating to obtain cDNA. Using this cDNA as a template, in the presence of dATP, dCTP, dGTP and dTTP, a double stranded DNA which is joined at an end is formed by a reverse transcriptase or a DNA polymerase I. The terminal joint of the thus obtained [DNA] *dATP* is cut by a nuclease $S_1$. In the presence of DATP, oligo (deoxyadenosine monophosphate) [hereinafter frequently referred to as "oligo [(dA)"]MD] (*dA*)"] is added to 3'-terminals of the above-obtained DNA by a terminal transferase. Meanwhile, a plasmid [pBr322] *pBR322* [F. Bolivar et al, "Construction and Characterization of New Cloning Vehicle: II. A Multipurpose Cloning System": *Gene*, November, 95 (1977)] is cleaved by restriction enzyme EcoRI and further treated with a λ-exonuclease. Subsequently, in the presence of dTTP, an oligo (dT) is ligated to 3'-terminals of the cleaved plasmid pBR322 by a terminal transferase. The aforementioned oligo (dA)-tailed double stranded DNA and the oligo (dT)-tailed linear plasmid are mixed and annealed. The annealed plasmid is inserted into E. coli strain X1776 [which is deposited with American Type Culture Collection (ATCC), Rockville, MD. U.S.A., as an accession number ATCC No. 31244] to transform the strain. The transformed strain is selected by the criterion of drug resistance such as ampicillin resistance. On the other hand, according to the same manner as mentioned above, mitogen-induced mRNA is prepared and labelled at the 5'-terminal by using a T4 polynucleotide kinase and [$\gamma$-$^{32}$P] ATP. To the [$^{32}$P]-labelled mRNA (hereinafter frequently referred to as $^{32}$p-mRNA") is added unlabelled mRNA in an amount about 200 times that of the labelled mRNA. The above-mentioned unlabelled mRNA is extracted from human peripheral blood lymphocytes which are not stimulated with a mitogen and, therefore, do not produce the physiologically active peptide of the present invention. Using the above-obtained mixture of mRNA as a probe, the transformed strain is determined by a colony hybridization method. In this method, the $^{32}$P-mRNA specifically hybridizes with cDNA which is formed by a template of mRNA which is present only in a mitogen induced cell capable of producing the peptide of the present invention and absent in an uninduced cell. The transformed strain having the cDNA which hybridizes with a $^{32}$P-mRNA is easily detected as a shadow on an autoradiogram. The transformed strain having a cDNA which hybridizes with a $^{32}$P-mRNA is denatured and DNA is recovered. The plasmid DNA containing the cDNA fragment is separated from the above-obtained DNA by ultracentrifugation. The thus obtained plasmid DNA is cleaved by a restriction enzyme PstI and then partially digested with BstNI. Subsequently, oligodeoxynucleotides prepared according to a well-known method [K. Itakura et al:Science, Vol. 198, p 1056 (1976),] of which the formulae are as follows:

AATTCATGTGTATC

GTCCTAGGCTCCCTC

GGCTGTTATTGTC

TGACAATA

ACAGCCGAGGGAGCC

TAGGACGATACACATG (wherein A, G, C and T are as defined before and wherein the left end of each formula and the right end of each formula represent 5'-hydroxyl group side and 3'-hydroxyl group side, respectively), are annealed to one another, whereby a double stranded oligomer having an initiation triplet codon ATG and having terminals cleaved by EcoRI and BstNI is prepared. The thus synthesized double stranded oligomer is ligated, by means of a T4 DNA ligase, to a cDNA fragment which is cleaved by restriction enzymes BstNI and PstI. The thus obtained DNA fragment is inserted between the sites of pBR322 cleaved by EcoRI and PstI.

Subsequently, a DNA fragment of 300 base pairs having a promoter, an operator and a ribosome binding site of a tryptophan operon of E. coli and having EcoRI-cleaved terminals is ligated to the cDNA fragment which is inserted to pBR322 at cleaved sites by EcoRI.

Then, the thus prepared plasmid is introduced into E. coli. According to the above-mentioned method, when the cDNA fragment is properly bonded to a promotor in the direction of the transcription, in a cell of E. coli, the cDNA begins to be transcripted to mRNA by the function of a promoter of an operon. Further, the transcripted mRNA begins to be translated into an amino acid at the initiation triplet codon, to give the intended peptide. Thus, one mg of the intended peptide can be extracted from cultured cells of E. coli in one liter of a culture medium.

The cells of E. coli which produce the intended peptide are collected after incubation and undergo bacteriolysis. Nucleic acids in the solution containing lysed cells are digested with a ribonuclease and a deoxyribonuclease and then, the intended peptide precipitates by salting-out with 65% saturation degree of ammonium sulfate. The precipitated fraction is purified by using controlled pore glass beads.

The method of determining the amino acid sequence of the novel physiologically active peptide of the present invention is as follows. First, methionyl bonds of the novel physiologically active peptide of the present invention are cut by cyanogen bromine. The cut fragments are separated by using Sephadex (manufactured and sold by Pharmacia Fine chemicals, Inc., Sweden) G-100 columns, and the amino acid sequence of each fragment is successively determined from the N-terminal by a well-known high precision amino acid sequence analysis. On the other hand, the novel physiologically active peptide of the present invention is partially digested with trypsin and then, the obtained fragments are separated by using Sephadex G-100 column. According to the same manner as described above, the amino acid sequence of each fragment is successively determined from the N-terminal. Making a comparison between the amino acid sequences of the fragments cut by cyanogen bromide and the amino acid sequences of the fragments digested with trypsin, the arrangement of fragments in the peptide is determined. Thus, the amino acid sequence of the novel physiologically active peptide of the present invention is determined.

For the inhibition of cell proliferation, e.g. malignant tumor cell proliferation, the peptide of the present invention may generally be administered by intravenous, intramuscular or hypodermic injection. The daily dosage of the peptide of the present invention will, naturally, vary depending on the age, condition and body weight of the patient. However, the peptide may normally be injection administered in an amount of about $1\times10^4$ to $1\times10^9$ units per day for adults.

For the treatment of viral induced disorders, an ointment containing about $1\times10^4$ to $1\times10^9$ units of the peptide of the present invention per 10 grams of the ointment is applied to the skin. Conventionally known pharmaceutically acceptable ointment bases may be used to prepare an ointment containing the peptide of the present invention. The daily dosage will, naturally, vary depending on the age and condition of the patient. However, the ointment containing the peptide of the present invention may be normally administered in divided applications so that the dosage is about $1\times10^4$ to $1\times10^9$ units as the peptide of the present invention.

The present invention will be illustrated in more detail with reference to the following Examples, which should not be construed as limiting the scope of the present invention.

ABBREVIATIONS USED IN THE EXAMPLES

ε-Z-lysine: a lysine having a benzyloxycarbonyl group(Z—) bonded to the ε-amino group of lysine G-$NO_2$-arginine:an arginine having a nitro group ($NO_2$—) bonded to the guanidino group(G—) of arginine imBzl-histidine:a histidine having a benzyl group (Bzl—) bonded to the imidazolyl group(im) of histidine O-Bzl-serine:a serine having a benzyl group(Bzl—) bonded to the hydroxyl group(O—) of serine Boc-valine a valine having a tert-butoxycarbonyl group (Boc—) bonded to the α-amino group of valine OBzl:an ortho-methyl benzyl group which is one of side chain protecting groups VSV:vesicular stomatitis virus dA:deoxyadenosine dC:deoxycytidine dG:deoxyguanosine dT:deoxyribosylthymine dbzA:deoxybenzyladenosine dibG:deoxyisobutylguanosine (DMTr)A:5'-dimethoxytrityladenosine (DMTr)T:5'-dimethoxytritylthymidine TNE:an aqueous solution containing 50 mM of Tris-HCl (pH 7.5), 100 mM of NaCl and 5 mM of ethylenediaminetetraacetic acid
AMV:avian myeloblastosis virus
dGTP:deoxyguanosine triphosphate
dAMP:deoxyadenosine monophosphate
BSA:bovine serum albumin
SEA:staphylococcal enterotoxin A which is one of mitogens
2×SSC:an aqueous solution containing 0.3 M NaCl and 0.03 M sodium citrate (pH 7)
4×SSC:an aqueous solution containing 0.6 M NaCl and 0.06 M sodium citrate
EDTA:ethylenediaminetetraacetic acid
SDS:sodium dodecyl sulfate
DTT:dithiothreitol (Cleland's reagent)

EXAMPLE 1

Step 1 (Washing of Resin)

150 g of a resin [Bio-Bead S-$X_2$, 200–400 mesh, (the trade name of 2% divinylbenzene-crosslinked styrene polymer, manufactured and sold by Bio-Rad Laboratories, U.S.A.)] is added to 1 liter of distilled benzene while stirring. 30 minutes later, the resin is filtered out with a glass filter and dried. Subsequently, the resin is added to 1 liter of methanol while stirring, and after 30 minutes, separated by filtration. The resin is washed with each of methanol, methanol/water and water successively. The washed resin is added to 1 liter of 1N aqueous NaOH. The mixture is stirred for one hour in a boiling water bath and subjected to filtration to collect the resin. The obtained resin is washed with water. Subsequently, the resin is added to 1 liter of 1N aqueous HCl. The mixture is stirred for one hour in a boiling water bath and subjected to filtration to collect the resin. The thus obtained resin is washed with water. The washed resin is suspended in 4 liters of distilled water. The resulting suspension is allowed to stand for 30 minutes and subjected to decantation to remove the floating minute resin. There is obtained resin as precipitates. The precipitated resin is taken on a glass filter by filtration and washed with methanol. The washed resin is added to a small amount of dimethylformamide (hereinafter frequently referred to as "DMF"). The mixture is stirred for 30 minutes at 80° C. and then, the resin is separated by filtration and washed with DMF and methanol. Further, the resin is stirred for one hour in 2 liters of methanol and then separated by filtration. The thus obtained resin is air-dried and further vacuum dried at 100° C. for 2 hours.

Step 2 (Preparation of Chloromethyl Resin)

25 g of the resin obtained according to the Step 1 and 100 ml of distilled chloromethyl methyl ether are put into a 1-liter three-necked flask and slowly stirred at 25° C. for 1 hour so that the resin is swollen, followed by cooling to 0° C. While stirring, 50 ml of a chloromethyl methyl ether solution containing 1.88 ml of $SnCl_4$ is gradually added to the swollen resin over 30 minutes at 0° C., and further stirred for 30 minutes to obtain a reaction product. The product thus obtained is separated by filtration with a glass filter and gently washed with 500 ml of dioxane-water (1:1) and subsequently with 500 ml of dioxane-3N aqueous HCl (3:1). Further, the product is sufficiently washed with water, dioxane-water and methanol and dried under reduced pressure at 100° C.

Step 3

A. (ε-Z-lysine)

10 g of $NaHCO_3$ and 12 ml of Z-Cl are added by quarters at intervals of 10 minutes to 11 g of a copper salt of L-lysine while stirring on ice, and further stirred for 3.5 hours. The resulting precipitate is filtered off, and washed with water, ethanol, and acetone/diethyl ether, successively. The precipitate is suspended in 250 ml of water and dissolved by addition of 412 ml of 6N aqueous HCl. Then, gaseous $H_2S$ is bubbled through the solution for one to two hours. The resulting CuS is filtered off using Hyflosupercel (Wako Junyaku Kogyo K.K., Japan). The cake is washed with 1N aqueous HCl. The filtrate and washings are collected and bubbled by air to remove $H_2S$. Subsequently, the solution is adjusted to pH 6.5 with concentrated aqueous ammonia on ice, and allowed to stand in a refrigerator for about two hours. The resulting precipitate is separated by filtration and washed with water, ethanol and diethyl ether, successively. Thus, there is obtained 10 g of ε-Z-lysine having a melting point of 254° C. The yield of the product is 65%. Recrystallization is performed by dissolving in diluted hydrochloric acid and neutralizing with aqueous ammonia.

B. (G-$NO_2$-arginine)

A mixture of 120 ml of fuming nitric acid and 75 ml of fuming sulfuric acid is ice-cooled and 110 g of L-arginine hydrochloride is added little by little to the mixture while stirring. Further, 45 ml of concentrated sulfuric acid is stirred to the mixture. The mixture is stirred for one hour, poured onto pieces of ice and adjusted to pH 8 with concentrated aqueous ammonia. Subsequently, the mixture is adjusted to pH 6 with acetic acid and allowed to stand in a refrigerator for about four hours. The resulting precipitate is filtered off and recrystallized from boiling water. Then, the crystals are washed successively with ethanol and diethyl ether, and dried.

Thus, there is obtained 60 g of G-$NO_2$-arginine having a melting point of 251° C. The yield of the product is 50%.

C. (imBzl-histidine)

20 g of L-histidine Hydrochloride-$H_2O$ is dissolved in 200 ml of liquid ammonia cooled to −30° C. in a bath of dry ice and acetone. Then, while stirring, pieces of metallic sodium are added to the solution until a blue color of the solution is maintained. Then, a small amount of histidine is added to the solution until the blue color disappears, and then benzyl chloride is added dropwise to the solution. The mixture is stirred for 30 minutes and subjected to evaporation at room temperature under atmospheric pressure and then under reduced pressure using a water-jet pump to remove $NH_3$. The resulting residue is poured in 100 ml of iced water. The mixture is extracted with diethyl ether, and the insoluble matter is removed by filtration. The resulting solution is adjusted to pH 8 by addition of a diluted $H_2SO_4$ and is allowed to stand in a refrigerator for three hours. The precipitate is filtered off and recrystallized from 70% by weight aqueous ethanol. As a result, there is obtained 13 g of imBzl-histidine having a melting point of 248° C. The yield of the product is 50%.

D. (O-Bzl-serine)

237 g of acetyl-L-serine is dissolved in 235 ml of 5N aqueous NaOH, and the solution is adjusted to pH 7.3. A solution made by dissolving 4 g of Takadiastase (manufactured and sold by Sankyo Co., Ltd., Japan) in 25 ml of 0.1 M aqueous citrate buffer (adjusted to pH 6.7, containing 0.025 M $CaCl_2$) is added and, after addition of several drops of toluene, the mixture is allowed to stand for ten days at 36° C., whereby a precipitate is formed. The precipitate is removed by filtration. The filtrate is concentrated, and acetone is poured in the filtrate to obtain a crystal. Thus, there is obtained 100 g of O-Bzl-serine. According to substantially the same manner as described above, there is obtained 100 g of O-Bzl-threonine from 240 g of acetyl-L-threonine.

E. (O-Bzl-tyrosine)

1.8 g of L-tyrosine and 1.2 g of $CuSO_4.5H_2O$ are suspended in a solution of 5 ml of 2N aqueous NaOH and 10 ml of water, and stirred for two hours. To the suspension is added 60 ml of methanol, and then gradually 1.2 ml of benzyl bromide and 0.7 ml of 2N aqueous NaOH. 15 minutes later, 0.3 ml of benzyl bromide and 0.8 ml of 2N aqueous NaOH are added. The mixture is stirred for one hour and subjected to filtration. The resulting precipitate is washed with methanol-water (1:3). Thus, 2 g of a copper salt of O-Bzl-tyrosine is obtained. The thus obtained copper salt of O-Bzl-tyrosine and 20 ml of a 1N aqueous solution of EDTA are mixed in a mortar with a pestle, and the mixture is subjected to filtration and the cake is washed with water. The product is recrystallized from hot water containing a small amount of ethylenediaminetetraacetic acid. Thus, there is obtained 1 g of O-Bzl-tyrosine having a melting point of 223° C. The yield of the product is 30%.

F. (S-Bzl-cysteine)

157 g of L-cysteine hydrochloride is dissolved in 2 liters of 2N aqueous NaOH. Then, while vigorously stirring on ice, 256 g of benzyl bromide is added to the solution, and the solution is stirred for five hours in a cold room. Then, the solution is adjusted to pH 5 by addition of acetic acid to form a precipitate. The precipitate is separated by filtration and washed with water. Thus, there is obtained 160 g of S-Bzl-cysteine having a melting point of 212° C. The yield of the product is 70%.

According to substantially the same manner as described above, there are obtained 150 g of O-Bzl-aspartic acid from 160 g of aspartic acid and 150 g of O-Bzl-glutamic acid from 160 g of glutamic acid.

G. (Boc-amino Acid)

29 g of L-valine is dissolved in 250 ml of 1N aqueous NaOH, and to the solution is added water so that 400 ml of the solution is obtained. To the solution is added 150 ml of tetrahydrofuran. Then, while vigorously stirring at 10° C., to the solution are added 100 ml of Boc-Cl by 1/5 amounts at intervals of ten minutes, while 2N aqueous NaOH is added after every addition of Boc-Cl in such amount as will provide a pH value of about 8 to 9. Two hours later, the mixture is extracted with diethyl ether. The aqueous layer is acidified with an aqueous solution of 0.5 M aqueous citric acid, whereby an oily substance is precipitated. The precipitate is extracted with ethyl acetate. The extract is washed with a small amount of water, dried over $Na_2SP_4$, and concentrated under reduced pressure. To the concentrated extract is added petroleum ether, and the mixture is allowed to stand in a refrigerator, whereby a crystal is formed. The crystal is filtered off and dried. Thus, there is obtained 30 g of Boc-valine having a melting point of 78° C. The yield of the product is 55%.

H. (Other Boc-Amino Acids)

Substantially the same procedures as described above are repeated to prepare 15 g of Boc-glycine, 16 g of Boc-alanine, 15 g of Boc-leucine, 15 g of Boc-isoleucine, 14 g of Boc-serine (Bzl), 14 g of Boc-threonine (Bzl), 15 g of Boc-cysteine (Bzl), 15 g of Boc-methionine, 12 g of Boc-proline, 15 g of Boc-aspartic acid (OBzl), 15 g of Boc-glutamic acid (OBzl), 15 g of Boc-glutamine, 12 g of Boc-histidine (Bzl), 13 g of Boc-lysine (Z), 15 g of Boc-arginine ($NO_2$), 15 g of Boc-phenylalanine, 15 g of Boc-tyrosine (Bzl) and 10 g of Boc-tryptophan, respectively from 30 g of glycine, 30 g of alanine, 30 g of leucine, 30 g of isoleucine, 30 g of serine (Bzl), 30 g of threonine (Bzl), 30 g of cysteine (Bzl), 30 g of methionine, 30 g of proline, 30 g of aspartic acid (OBzl), 30 g of glutamic acid (OBzl), 30 g of glutamine, 30 g of histidine (Bzl), 30 g of lysine (Z), 30 g of arginine ($NO_2$), 30 g of phenylalanine, 30 g of tyrosine (Bzl) and 30 g of tryptophan.

Step 4 (Bonding of Boc-Glutamine to Resin)

A mixture of 2 g of the chloromethyl resin (Cl total content: 4 mmol), 2 mmol of Boc-L-glutamine, 1.8 mmol of triethyl amine and 12 ml of dimethylformamide is agitated at room temperature for 24 hours. The mixture is filtered through a glass filter, and the solid product is washed with 700 ml each of dimethylformamide, ethanol, acetic acid/ethanol and methylene chloride successively. The product is dried under reduced pressure at room temperature. To determine the amino acid content, 50 mg is weighed out from the product, hydrolyzed in a 1:1 by volume mixture of 12N aqueous HCl and dioxane for 24 hours, and subjected to an amino acid analyzer. The amino acid content is 0.2 mmol/g.

Step 5 (Boc-Ser-Gln Resin)

2 g of the Boc-Gln Resin obtained in Step 4 is put in 160 ml of acetic acid and allowed to stand for 6 hours at room temperature. The mixture is filtered with a glass filter. The cake is put in 160 ml of acetic acid, agitated and filtered. This operation is repeated three times. Then, the cake is agitated in 160 ml of 1N aqueous HCl/acetic acid at room temperature for half an hour to remove the Boc group from the resin. The resulting product is filtered off, washed with three portions of each of acetic acid, ethanol and dimethylformamide successively, and agitated in 160 ml of a 10% by weight solution of triethylamine in dimethylformamide to effect neutralization reaction. The resulting product is filtered off and washed with each of dimethylformamide and methylene chloride. The product is immersed in a solution made by adding 2 mmol of Boc-serine (Bzl) to 12 ml of methylene chloride, and agitated. Ten minutes later, a solution made by adding 20 mmol of dicyclohexyl carbodiimide to 60 ml of methylene chloride is added to the mixture and agitated at room temperature for 2 hours to effect coupling reaction. The resulting product is filtered off and washed with each of methylene chloride and ethanol.

Step 6 (Boc-Peptidyl Resin)

By repeating substantially the same procedures as described in Step 5 above to elongate the amino acid chain, the following Boc-peptidyl resins are obtained:

Boc-HC*(0)-resin,

Boc-HC*(−121, −126, −127, −133, −136, −150, −151)-resin,

Boc-HC*(−121, −126, −127, −133, −136)-resin,

Boc-HC*(−150, −151)-resin,

Boc-
HC*(+121, +126, +127, +133, +136, +150, +151)-resin,
Boc-HC*(+121, +126, +127, +133, +136)-resin,
Boc-HC*(+150, +151)-resin,
Boc-MC*(0)-resin,
Boc-
MC*(−121, −126, −127, −133, −136, −150, −151)-resin,
Boc-MC*(−121, −126, −127, −133, −136)-resin,
Boc-MC*(−150, −151)-resin
Boc-
MC*(+121, +126, +127, +133, +136, +150, +151)-resin,
Boc-MC*(+121, +126, +127, +133, +136)-resin, and
Boc-MC*(+150, +151)-resin, wherein [M*] *MC** represents methionyl, HC* HC*(0) represents Cys (Bzl) Ile Val Leu Gly Ser (Bzl) Leu Gly Cys (Bzl) Tyr (Bzl) Cys (Bzl) Gln Asp (OBzl) Pro Tyr (Bzl) Val Lys (Z) Glu (OBzl) Ala Glu (OBzl) Asn Leu Lys (Z) Lys (Z) Tyr (Bzl) Phe Asn Ala Gly His (Bzl) Ser (Bzl) Asp (OBzl) Val Ala Asp (OBzl) Asn Gly Thr (Bzl) Leu Phe Leu Gly Ile Leu Lys (Z) Asn Trp Lys (Z) Glu (OBzl) Glu (OBzl) Ser (Bzl) Asp (OBzl) Arg ($NO_2$) Lys (Z) Ile Met Gln Ser (Bzl) Gln Ile Val Ser (Bzl) Phe Tyr (Bzl)Phe Lys (Z) Leu Phe Lys (Z) Asn Phe Lys (Z) Asp (OBzl) Asp (OBzl) Gln Ser (Bzl) Ile Gln Lys (Z) Ser (Bzl) Val Glu (OBzl) Thr (Bzl) Ile Lys (Z) Glu (OBzl) Asp (OBzl) Met Asn Val Lys (Z) Phe Phe Asn Ser (Bzl) Asn Lys (Z) Lys (Z) Lys (Z) Arg ($NO_2$) Asp (OBzl) Asp (OBzl) Phe Glu (OBZl) Lys (Z) Leu Thr (Bzl) Asn Tyr (Bzl) Ser (Bzl) Val Thr (Bzl) Asp (OBzl) Leu Asn Val Gln Arg ($NO_2$) Lys (Z) Ala Ile His (Bzl) Glu (OBzl) Leu Ile Gln Val Met Ala Glu (OBzl) Leu Ser (Bzl) Pro Ala Ala Lys (Z) Thr (Bzl) Gly Lys (Z) Arg ($NO_2$) Lys (Z) Arg ($NO_2$) Ser (Bzl) Gln Met Leu Phe Arg ($NO_2$) Gly Arg ($NO_2$) Arg ($NO_2$) Ala Ser (Bzl) Gln, in which the symbols have the same meaning as defined hereinbefore, the minus(−) -marked number in the parentheses indicates that an amino acid is absent on the Boc-peptide resin at that number of amino acid residues from the carboxyl end group of HC*(0), and the plus(+) -marked number in the parentheses indicates that glycine is bonded to the amino group of the amino acid residue at that number from the carboxyl end group of HC*(0). *The amino acid sequence of the HC* (0) apparently consists of the amino acid sequence of Cys Ile Val Leu Gly Ser Leu Gly Cys Tyr Cys and the amino acid sequence of the formula (II), namely, Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln, which amino acid sequence of the formula (II) is one that has been built through extension of the amino acid chain as mentioned above.*

Step 7 (Cleavage from Resin, of HC and MC which differ from HC* and MC* in that HC and MC have no protective groups whereas HC* and MC* have protective groups)

Charged into a reaction vessel having a polytetrafluoroethylene-covered stirrer are 1.4 g of the Boc-HC*(0)-resin obtained in Step 6 above and 1 ml of anisole. 20 ml of hydrogen fluoride is introduced into the reaction vessel while cooling in dry ice/acetone, stirred at 0° C. for one hour, and evaporated at 0° C. under reduced pressure to remove hydrogen fluoride. The resulting HC(0) peptide is isolated by adding 1% by weight aqueous acetic acid to the residue while stirring, thereby to extract the peptide, followed by washing in a separatory funnel with diethylether and lyophilizing.

By [repeating] *effecting* substantially the same procedures as described above, the following peptides (each 150 mg) are obtained from the Boc-peptidyl resins as obtained in Step 6 above:

HC(−121, −126, −127, −133, −136, −150, −151),
HC(−121, −126, −127, −133, −136),
HC(−150, −151),
HC(+121, +126, +127, +133, +136, +150, +151),
HC(+121, +126, +127, +133, +136),
HC(+150, +151),
MC(0),
MC(−121, −126, −127, −133, −136, −150, −151),
MC(−121, −126, −127, −133, −136),
MC(−150, −151),
MC(+121, +126, +127, +133, +136, +150, +151),
MC(+121, +126, +127, +133, +136), and
MC(+150, +151).

Step 8 (Analytical Data on Synthesized Peptides)

The peptides obtained in Step 7 above are subjected to measurement of the molecular weight of each peptide and determinations of the amino acid composition and amino acid sequence for each peptide.

The molecular weight of each peptide is calculated from the mobility as measured by SDS gel electrophoresis.

The molar percent amino acid composition is determined by hydrolyzing an aliquot of each peptide in 6N aqueous HCl at 110° C. for 24 hours and subjecting the resulting mixture to planar paper chromatography. In this analysis, tryptophan, cystine and cysteine cannot be identified. Another aliquot of each peptide is digested using a proteolytic enzyme to determine the concentration of each of tryptophan, cystine and cysteine. Glutamic acid cannot be distinguished from glutamine, and aspartic acid cannot be distinguished from asparagine.

The amino acid sequence of each peptide is determined by the automatic amino acid analyzer manufactured and sold by Hitachi, Ltd., Japan.

1. Peptide HC(0)

Molecular Weight: about 20,000 g/mol

Amino Acid Composition (molar percent): histidine (1.3) tryptophan (0.3) lysine (13.0) arginine (5.2) aspartic acid/asparagine (13.0) serine (7.8) glutamic acid/glutamine (11.6) threonine (3.2) glycine (4.5) proline (1.3) alanine (5.2) valine (5.8) ½ cystine (2.0) methionine (2.6) isoleucine (5.2) leucine (7.8) phenylalanine (6.5) tyrosine (3.3)

Amino Acid Sequence: Cys Ile Val Leu Gly Ser Leu Gly Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln.

2. Peptide HC(−121, −126, −127, −133, −136, −150, −151)

Molecular Weight: about 20,000 g/mol

Amino Acid Composition (molar percent): (Only amino acids having a significantly different concentration as compared with HC(0) are indicated. This is true for the following HC peptides.)

glycine (3.4) alanine (3.4) leucine (6.8)

3. Peptide HC(−121, −126, −127, −133, −136)

Molecular Weight: about 20,000 g/mol

Amino Acid Composition (molar percent): glycine (4.0) alanine (3.4) leucine (7.4)

4. Peptide HC(−150, −151)

Molecular Weight: about 20,000 g/mol

Amino Acid Composition (molar percent): glycine (3.9) leucine (7.2)

5. Peptide HC(+121, +126, +127, +133, +136, +150, +151)

Molecular Weight: about 20,000 g/mol

Amino Acid Composition (molar percent): glycine (8.7)

6. Peptide HC(+121, +126, +127, +133, +136)

Molecular Weight: about 20,000 g/mol

Amino Acid Composition (molar percent): glycine (7.5)

7. Peptide HC(+150, +151)

Molecular Weight: about 20,000 g/mol

Amino Acid Composition (molar percent): glycine (5.8)

8. Peptide MC(0)

Molecular Weight: about 20,000 g/mol

Amino Acid Composition (molar percent): histidine (1.3) tryptophan (0.3) lysine (12.9) arginine (5.2) aspartic acid/asparagine (12.9) serine (7.7) glutamic acid/-glutamine (11.6) threonine (3.2) glycine (4.5) proline (1.1) alanine (5.2) valine (5.8) ½ cystine (1.9) methionine (3.2) isoleucine (5.2) leucine (7.7) phenylalanine (6.5) tyrosine (3.2)

Amino Acid Sequence: Met Cys Ile Val Leu Gly Ser Leu Gly Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln 9. Peptide MC(−121, −126, −127, −133, −136, −150, −151)

Molecular Weight: about 20,000 g/mol

Amino Acid Composition (molar percent): (Only amino acids having a significantly different concentration as compared with MC(0) are indicated. This is true for the following MC peptides.) glycine (3.4) alanine (3.4) leucine (6.8)

10. Peptide MC(−121, −126, −127, −133, −136)

Molecular Weight: about 20,000 g/mol

Amino Acid Composition (molar percent): glycine (4.0) alanine (3.3) leucine (7.3)

11. Peptide MC(−150, −151)

Molecular Weight: about 20,000 g/mol

Amino Acid Composition (molar percent): glycine (3.9) leucine (7.2)

12. Peptide MC(+121, +126, +127, +133, +136, +150, +151)

Molecular Weight: about 20,000 g/mol

Amino Acid Composition (molar percent): glycine (8.6)

13. Peptide MC(+121, +126, +127, +133, +136)

Molecular Weight: about 20,000 g/mol

Amino Acid Composition (molar percent) glycine (7.5)

14. Peptide MC(+150, +151)

Molecular Weight: about 20,000 g/mol

Amino Acid Composition (molar percent): glycine (5.7)

Step 9 (Measurement of Antiviral Activity)

The antiviral activity of each peptide as obtained in Step 7 is measured in substantially the same manner as described in P. C. Merigan, A Plaque Inhibition Assay for Human Interferon Employing Human Neonate Skin Fibroblast Monolayers & Bovine Vesicular Stomatitis Virus, "In-vitro Method in Cell-Mediated Immunity," edited by E.D.B.R. Bloom & P.R. Grade, Academic Press, N.Y., 1971, pp489.

Specifically, each peptide as obtained in Step 7 is diluted and added to a growth medium containing 10% by volume of fetal calf serum. In the growth medium, a mono-layer of (Human Neonate Skin [Filbroblast] *Fibroblast*) is cultured. Eighteen hours later, infection with vesicular stomatitis viruses which are each capable of forming 20 plaques per cell is effected, and culturing is continued at 37° C. for one hour. Then, the cells are rinsed with two portions of the above-mentioned growth medium. Again, the cells are cultured in the growth medium at 37° C. for 24 hours. Generation of viruses is checked by microscopic observation of the cells. Any damage of the cells is ascribed to viruses. The following peptides, at 1 μg/ml, show antiviral activity:

HC(0),
HC(−121, −126−127, −133, −136, −150, −151)
HC(−121, −126, −127, −133, −136),
HC(−150, −151),
HC(+121, +126, +127, +133, +136, +150, +151),
HC(+121, +126, +127, +133, +136),
HC(+150, +151),
MC(0),
MC(−121, −126, −127, −133, −136, −150, −151),
MC(−121, −126, −127, −133, −136),
MC(−150, −151),
MC(+121, +126, +127, +133, +136, +150, +151),
MC(+121, +126, +127, +133, +136), and
MC(+150, +151).

Step 10 (Measurement of Cell Growth Inhibition Action)

$2\times10^5$ FS-4 cells are transplanted into a growth medium as defined in Step 9 above which is contained in a petri dish of 60 mm in diameter. Five hours later, the growth medium is removed. Then, a fresh growth medium containing peptide HC(0) or above peptide MC(0) as obtained in Step 7 above in a concentration of 0.1

μg/ml is poured in the petri dish, and culturing is continued at 37° C. for 18 hours. The medium is removed and a fresh growth medium containing 3H-thymidine in a concentration of 5 μCi/ml is added, followed by culturing at 37° C. for 2 hours. The cells are rinsed with phosphate-buffered saline, and 5% by weight aqueous trichloroacetic acid is added. An aliquot of the resulting deposit is dried and subjected to measurement of the $^3$H-adioactivity by means of a liquid scintillation counter manufactured and sold by Packard Instrument Company, Inc., U.S.A. For comparison, peptides respectively having the same amino acid sequences of pro-IFN-γ, IFN-γ and IFN-γ-like peptide elucidate by David V Goeddel are prepared according to the solid phase synthetic method described hereinbefore, and subjected to the above-described measurement of cell growth inhibition action.

| Material | Amount μg/ml | In-take of Thymidine cpm | % |
|---|---|---|---|
| None | — | 2500 | 100 |
| HC(0) | 0.1 | 200 | 8 |
| MC(0) | 0.1 | 200 | 8 |
| pro-IFN-γ | 0.1 | 2500 | 100 |
| IFN-γ | 0.1 | 2000 | 80 |
| IFN-γ like peptide | 0.1 | 2000 | 80 |

It is seen that the peptides HC(0) and MC(0) of the present invention are very effective in cell growth inhibition action, that pro-IFN-γ has no capability of cell growth inhibition, and that IFN-γ and IFN-γ-like peptide have a low activity of cell growth inhibition.

EXAMPLE 2

Step 1. (Benzoylation or isobutylation)

A. Synthesis of dbzA 50 mmol of deoxyadenosine (dA) is suspended in 150 ml of dry pyridine. 300 mmol of benzoylchloride is added dropwise while ice-cooling and then, the reaction mixture is warmed to room temperature, followed by stirring for about one hour. The completion of the reaction is confirmed by means of thin-layer chromatography (TLC) (eluent:a 10:1 by volume mixture of chloroform and methanol). The reaction mixture is then poured into a mixture of 500 ml of chloroform, 350 g of ice and 28 g of sodium hydrogen carbonate. The resulting mixture is shaken in a separatory funnel, and the chloroform phase is taken out. The aqueous phase is extracted with two portions of chloroform, and the chloroform phase is taken out. The chloroform phases obtained are mixed together and washed with two portions of water. Chloroform is distilled off, and 150 ml of ethanol and 100 ml of pyridine are added to the residue to obtain a homogeneous solution. The thus obtained homogeneous solution is chilled quickly to 0° C., and a mixture of 200 ml of 2N aqueous NaOH and 200 ml of ethanol is added while stirring to the solution, thereby to obtain a homogeneous solution. The resulting solution is stirred at room temperature for 5 minutes, cooled, and, after addition of 200 ml of 2N aqueous hydrochloric acid, concentrated to half volume under reduced pressure. Thereafter, an equal amount of water is added to the thus concentrated solution, and benzoic acid is extracted out with diethyl ether. The aqueous phase is concentrated and subjected to azeotropic distillation with water, whereby N-benzoyl deoxyadenosine (dbzA) is deposited. A small amount of pyridine is added to the thus obtained N-benzoyl deoxyadenosine, and the resulting mixture is, after allowed to stand overnight in a refrigerator, subjected to filtration, whereby deposited crystals are filtered off. The crystals thus isolated are washed with a 5% by weight aqueous pyridine solution, and then with diethyl ether. As a result, 35 mmol of dbzA is obtained. The total yield of dbzA is 70%.

B. Synthesis of dbzC 100 mmol of deoxycytidine (dC) is suspended in 500 ml of pyridine, 1 equivalent of triethylamine is added to the resulting suspension, followed by stirring for 30 minutes. 6 equivalents of benzoyl chloride is then added with ice-cooling. Subsequently, the same procedures as employed in item A above are repeated, whereby benzoylation of dC is attained. The residue left after removal of chloroform is dissolved in a mixture of 1250 ml of tetrahydrofuran, 1 liter of methanol and 250 ml of water. 250 ml of 2N NaOH is added to the resulting solution with stirring while ice-cooling. After 10 minutes, the mixture is neutralized by addition of 250 ml of 2N aqueous HCl. The subsequent procedures are the same as in item A. As a result, N-benzoyl deoxycytidine (dbzC) is deposited.

C. Synthesis of dibG 100 mmol of deoxyguanosine (dG) is suspended in 500 ml of pyridine. 6 equivalents of isobutyl chloride is added dropwise with ice-cooling. The so obtained reaction mixture is, after being stirred at 0° C. for 3 hours, subjected to the same treatment as employed in item B above, whereby isobutylation of dG is attained. The residue left after removal of chloroform is dissolved in 500 ml of ethanol, and then 500 ml of 2N NaOH is added at 0° C., followed by stirring for 15 minutes. The resulting mixture is then poured onto 1 liter of a chilled, pyridinium type cation exchange resin (Dowex×50×2, manufactured and sold by Dow Chemical Co., U.S.A.), whereby neutralization is effected. The thus neutralized mixture is placed in a column packed with a small amount of the above-mentioned resin, and washed with a 10% (w/v) aqueous pyridine solution of which the volume is 3-fold the volume of the packed resin. The eluate and the washings are mixed and concentrated, and the residue is recrystallized from 500 ml of a 5% (w/v) aqueous pyridine solution.

Step 2 (5'-dimethoxytritylation)

100 mmol of thymidine, 100 mmol of dbzA, 100 mmol of dbzC and 100 mmol of dibG are mixed with 200 ml, 400 ml, 400 ml and 750 ml of pyridine, respectively. Into each of the resulting mixtures, 1.1 equivalents of dimethoxytrityl chloride are added, and reaction is allowed to proceed for 3 hours. The reaction is stopped by adding 50 ml of methanol. Each of the reaction mixtures is concentrated, dissolved in 50 ml of chloroform, and washed with water. For isolation of 5'-dimethoxytritylthymidine[(DMTr)T], the reaction mixture is subjected to evaporation to remove the solvent, and then subjected to azeotropic distillation with toluene, dissolved in 1500 ml of benzene, heated, charged with n-hexane until the mixture becomes opaque, and allowed to stand at 4° C. to obtain recrystallized (DMTr)T. For isolation of (DMTr)dbzA, (DMTr)dbzC and (DMTr)dibG, each reaction mixture is subjected to evaporation to remove the solvent, dissolved in chloroform, and subjected to chromatography employing 1.5 kg of silica gel, in which elution is performed with a 3% by weight aqueous methanol.

Step 3(Synthesis of a dimer and a trimer)

6 mmol of (DMTr)dG is subjected to azeotropic distillation with pyridine and then dissolved in 10 ml of pyridine. 1.5 equivalents of p-chlorophenyl phosphorodichloride is added dropwise, with stirring on ice, to a mixture of 1.5×2.2 equivalents of triazole, 1.5×2.2 equivalents of triethylamine and 20 ml of dioxane, while avoiding moisture. After stirring for one hour at room temperature, triethylamine hydrochloride is filtered out. The filtrate is added to the above-obtained pyridine solution, while avoiding moisture. After evaporation-removal of approximately ¼ the volume of the solvent, the solution is allowed to stand for one hour at room temperature. Then, 4 equivalents of 1-methylimidazole and 8 mmol of dibG are added, and the resulting mixture is subjected to azeotropic distillation with pyridine. The residue is dissolved in 60 ml of pyridine. 9 mmol of TPS-nitroimidazolide(TPSNI) is charged in the thus obtained pyridine solution. The resulting mixture is concentrated to a ¼ volume, and then allowed to stand overnight at 30° C.

The reaction is stopped by addition of 6 ml of a 50 wt % aqueous pyridine solution. After evaporation-removal of the solvent, the mixture is passed through a column packed with 150 g of Type 60 silica gel (manufactured and sold by Wako Junyaku Kogyo, K.K., Japan). The developed product is eluted with a 30:1 by volume mixture of methylene chloride and methanol (pyridine content: 1%). The eluate is concentrated, and then charged with n-hexane, whereby a desired dimer is deposited in the form of a powder.

2 mmol of the thus obtained dimer is phosphated in substantially the same manner as mentioned above. 3 mmol of thymidine is added to the thus phosphated dimer, and the resultant is then subjected to azeotropic distillation with pyridine. The residue is dissolved in 20 ml of pyridine. 3 ml of TPSNI is charged to the resulting pyridine solution, and condensation is effected in the same manner as mentioned above. 21 hours later, the reaction is stopped by addition of 2 ml of a 50% by weight aqueous pyridine solution. 20 ml of chloroform is added, and the reaction mixture is washed twice with 15 ml of 0.1 M aqueous TEAB. After evaporation-removal of the solvent, the desired trimer is isolated by the use of 60 g of silica gel. The total yield of the trimer is 60%.

Step 4 (removal of protective group from the trimer)

20 mg of the trimer obtained in Step 3 above is dissolved in 3 ml of pyridine. 15 ml of concentrated aqueous ammonia is put in the above-obtained pyridine solution, stoppered, and then allowed to stand for 19 hours at room temperature. Thereafter, the reaction mixture is heated at 55° C. for 5 hours, to distill off the ammonia. Further, 20 ml of 80% by volume aqueous acetic acid is added to the reaction mixture, and then acetic acid is distilled off. The reaction mixture is then subjected to azeotropic distillation with toluene, and the residue is dissolved in 25 ml of 0.1 M aqueous TEAB, and washed with 25 ml of $CHCl_3$ three times and then with 25 ml of diethyl ether. The resulting solution is subjected to evaporation to remove the solvent, and the residue is dissolved in 16 ml of 7 M urea containing 20 mM Tris-$CH_3COOH$ (pH 8.0). The thus obtained mixture is passed through a column packed with DEAE cellulose, and eluted with a 7 M urea—0.02 M Tris-HCl (pH 8) eluent with a salt gradient (using 500 ml of 0.05 M NaCl and 500 ml of 0.40 M NaCl). The eluate fractions each exhibiting peak absorbance are collected, whereby the trimer is obtained.

Step 5 (Synthesis of oligonucleotide)

Oligodeoxyribonucleotides are prepared in the same manner as mentioned in Step 3. The protective groups are removed in the same manner as mentioned in Step 4, thereby to obtain the following oligodeoxyribonucleotides.

(1) G A T C C A T G T G T A T C G T T
(2) T T G G G T T C T T T G
(3) G G T T G T T A C T G T
(4) C A A G A C C C A T A C
(5) G T T A A G G A A G C T
(6) G A A A A C T T G A A G
(7) A A G T A C T T T A A C
(8) G C T G G T C A C T C T
(9) G A C G T T G C T G A C
(10) A A C G G T A C T T T G
(11) T T T T T G G G T A T C
(12) T T G A A G A A C T G G
(13) A A G G A A G A A T C T
(14) G A C A G A A A G A T C
(15) A T G C A A T C T C A A
(16) A T C G T T T C T T T T
(17) T A C T T T A A G T T G
(18) T T T A A G A A C T T T
(19) A A G G A C G A C C A A
(20) T C T A T C C A A A A G
(21) T C T G T T G A A A C T
(22) A T C A A G G A A G A C
(23) A T G A A C G T T A A G
(24) T T T T T T A A C T C T
(25) A A C A A G A A G A A G
(26) A G A G A C G A C T T T
(27) G A A A A G T T G A C T
(28) A A C T A C T C T G T T
(29) A C T G A C T T G A A C
(30) G T T C A A A G A A A G
(31) G C T A T C C A C G A A
(32) T T G A T C C A A G T T
(33) A T G G C T G A A T T G
(34) T C T C C A G C T G C T
(35) A A G A C T G G T A A G
(36) A G A A A G A G A T C T
(37) C A A A T G T T G T T T
(38) A G A G G T A G A A G A
(39) G C T T C T C A A T A A G
(40) T C G A C T T A T T G A G A A G C T C T T C T
(41) A C C T C T A A A C A A
(42) C A T T T G A G A T C T
(43) C T T T C T C T T A C C
(44) A G T C T T A G C A G C
(45) T G G A G A C A A T T C
(46) A G C C A T A A C T T G
(47) G A T C A A T T C G T G
(48) G A T A G C C T T T C T
(49) T T G A A C G T T C A A
(50) G T C A G T A A C A G A
(51) G T A G T T A G T C A A
(52) C T T T T C A A A G T C
(53) G T C T C T C T T C T T
(54) C T T G T T A G A G T T
(55) A A A A A A C T T A A C
(56) G T T C A T G T C T T C
(57) C T T G A T A G T T T C

(58) A A C A G A C T T T T G
(59) G A T A G A T T G G T C
(60) G T C C T T A A A G T T
(61) C T T A A A C A A C T T
(62) A A A G T A A A A A G A
(63) A A C G A T T T G A G A
(64) T T G C A T G A T C T T
(65) T C T G T C A G A T T C
(66) T T C C T T C C A G T T
(67) C T T C A A G A T A C C
(68) C A A A A A C A A A G T
(69) A C C G T T G T C A G C
(70) A A C G T C A G A G T G
(71) A C C A G C G T T A A A
(72) G T A C T T C T T C A A
(73) G T T T T C A G C T T C
(74) C T T A A C G T A T G G
(75) G T C T T G A C A G T A
(76) A C A A C C C A A A G A
(77) A C C C A A A A C G A T A C A C A T G

Step 6 (Sythesis of polynuceotide)

40 pico M each of the oligonucleotides (1) and (2) obtained in Step 5 above and 6.5 units of T4DNA kinase are put in 25 μl of a mixture of 80 pico M of [$\gamma$-$^{32}$P]ATP (8 Ci/mmol), 100 μM spermidine, 20 mM DTT, 10 mM $MgCl_2$, 50 mM Tris-HCl (pH 9) and 0.1 mM EDTA. The reaction is allowed to proceed for 30 minutes at 37° C., whereby (1) and (2) are bonded to obtain (1)–(2). Ethanol is added to the reaction mixture in a volume 2.5 times that of the reaction mixture, causing the oligomer to precipitate. Electrophoresis is effected on a 20% polyacryloamide gel in 7 M urea, therby to attain separation of (1)–(2).

(1)–(2) G A T C C A T G T G T A T C G T T T T G G G T T C T T T G (3) and (4) are bonded in the same manner as mentioned above, thereby to obtain (3)–(4). Separation of (3)–(4) is effected in the same manner as mentioned above. Further, the above-obtained (1)–(2) and (3)–(4) are bonded, to thereby to obtain (1)–(2)–(3)–(4). This operation is repeated, whereby the following DNA is obtained.

(1)-(2)-(3)-(4)-(5)-(6)-(7)-(8)-(9)-(10)-(11)-(12)-(13)-(14)-(15)-(16)-(17)-(18)-(19)-(20)-(21)-(22)-(23)-(24)-(25)-(26)-(27)-(28)-(29)-(30)-(31)-(32)-(33)-(34)-(35)-(36)-(37)--(38)-(39)
(40)-(41)-(42)-(43)-(44)-(45)-(46)-(47)-(48)-(49)-(50)-(51)--(52)-(53)-(54)-(55)-(56)-(57)-(58)-(59)-(60)-(61)-(62)-(63)-(64)-(65)-(66)-67)-(68)-(69)-(70)-(71)-(72)-(73)-(74)-(75)-(76)-(77)

(1)~(39) and (40)~(77) are mixed in a 50 μl TNE buffer solution. The mixture is incubated for one hour at a temperature of each of 65° C., 45° C., 37° C. and 20° C. Then, into the mixture is added a 20 μl mixture containing 100 mM Tris-HCl (pH 7.5), 100 mM $CaCl_2$ and 100 mM $MgCl_2$, followed by cooling on ice for 20 minutes.

Step 7 (Cloning)

In accordance with the procedure described in A. J. Twigg et al., Nature, 283, 216–217 (1980), pAT 153 plasmid is prepared. From the thus obtained pAT 153 plasmid, pPM 50 plasmid having a lac promoter and a lac operator is produced according to the procedure described in Michael D. Edge et al., Nature, 292, 756 (1981). 4 μg of pPM 50 plasmid DNA is cleaved in a mixture of 10 mM Tris-HCl (pH 7.6), 6 mM $MgCl_2$, 150 mM NaCl and 1 mM DDT for 60 minutes at 37° C. with restriction enzymes, BamHI and Sal I. After termination of the reaction, DNA is extracted with a 3:1 by volume mixture of phenol and chloroform, and fragments are separated by electrophoresis effected on a 1% agarose gel in a mixture of 40 mM Tris-HCl (pH 7.8), 6 mM sodium acetate and 1 mM EDTA. The large fragment is recovered, 1 μg of the so obtained BamHI-Sal I 3.2 kb vector fragment and the chemically synthesized gene obtained in Step 6 above are ligated in 30 μl of a mixture of 20 mM Tris-HCl (pH 7.6), 10 mM $MgCl_2$ and 10 mM DTT, containing 0.4 unit of T4 DNA ligase. The reaction is allowed to proceed for 16 hours at 12° C. As a result, there is obtained a plasmid containing DNA in which the chemically synthesized gene obtained Step 6 above is bonded to the end of the lactose operon.

The thus obtained plasmid is contacted with E. coli X 1776, thereby to transform the E. coli X 1776. The resulting transformants are cultured to prepare DNA. The thus prepared DNA is analyzed with respect to the DNA deoxyucleotide sequence in accordance with the procedure described in A. M. Maxam et al., Proc. Natl. Acad. Sci. U.S.A., 74, 560–564 (1978). The result shows that the analyzed sequence agrees with the theoretical sequence. The antiviral activity of the liquid culture medium of the transformants is examined by employing FS-4 cells and VSV as the challenge virus (FS-4 cells and VSV are employed in Example 1, Step 9). The result shows that this liquid culture medium exhibits antiviral activity (a series of experiments started with the insertion of the plasmid to the E. coli X 1776 are conducted in the P-3 containment facility of Asahi Kasei Kogyo, K.K.).

EXAMPLE 3

Step 1 (Construction of mRNA)

To 10 liter of a liquid culture medium containing lymphocytes adjusted to have a lymphocyte concentration of $1\times10^6$ cells/ml, 1 mg of staphylococcal enterotoxin A (SEA) is added, and the resultant is cultured with rotation for 2 days at 37° C. The lymphocyte is centrifuged for 10 minutes with a low revolution speed centrifuge of which the revolution speed is 800 rpm. The lymphocyte thus collected is resuspended in 1 liter of an aqueous solution of 8 g of NaCl, 0.2 g of KCl, 1.15 g of $Na_2PO_2.2H_2O$ and 0.2 g of $KH_2PO_4$, which solution is referred to as "PBP solution". The resulting suspension is, with vigorous stirring, added to 17 liter of a mixture of 20 mM Tris-HCl (pH 7.5) and 1 mM EDTA (the mixture of Tris-HCl and EDTA is hereinafter referred to as "TE buffer solution") containing 2% (w/v) sodium dodecyl sulfate (SDS), which is placed in a separatory funnel having a capacity of 50 liter. Pronase (manufactured and sold by Calbiochem., U.S.A.) is incorporated to a concentration of 200 μg/ml. followed by stirring at room temperature for one hour. Further, 2 M Tris-HCl (pH 9) is added in a volume 1/20 that of the above-obtained mixture, and the resultant is extracted with 15 liter of redistilled phenol for 20 minutes with vigorous stirring. Three liters of chloroform is then added, followed by stirring for 10 minutes. The phases of the resulting mixture are allowed to separate for one hour, and then the aqueous phase is removed by extraction with phenol and chloroform. To 18 liter of the thus obtained aqueous phase, 60 g of SDS is added. From the resulting mixture, a nucleic acid is precipitated with 3 M sodium acetate (pH 5.5) of which the volume is 1/10 the volume of the mixture, and with ethanol of which the volume is double the volume of the mixture. The thus treated mixture is allowed to stand at −20° C. overnight, and the supernatant is removed carefully by means of a syphon. The remaining portion is centrifuged at −20° C. for 15 minutes at a rate of 4000 rpm, whereby a nucleic acid precipitate is obtained. The thus obtained precipitate is put in 200 ml of a mixture of 50 mM Tris-HCl (pH 7.5), 100 mM NaCl and 5 mM EDTA (the mixture is hereinafter referred to as "TNE"), containing 0.5% (w/v) SDS, followed by stirring. Further, 350 ml of TNE is added to the above-obtained mixture so that the fibrous nucleic acid precipitate is dissolved. The resultant is centrifuged at 5000 rpm for 15 minutes, whereby the precipitate is collected. The thus collected precipitate is dissolved in 350 ml of TNE containing 0.5% (w/v) of SDS. The above-obtained two TNE solutions are mixed, and extracted with three portions of an equal volume of phenol, three portions of half volume of diethyl ether and three portions of an equal volume of diethyl ether. The recovered RNA is quantitated by adsorbance at 260 mμ on a spectrophotometer, and found to be approximately 100 mg.

27 g of Type 7 oligo(dT)cellulose (manufactured and sold by P&L Biochemicals, Inc., U.S.A.) is added to 500 ml of the above-obtained RNA-containing solution. The resulting mixture is stirred for one hour at room temperature, thereby causing the oligo(dT)cellulose to be adsorbed by mRNA. The oligo(dT)cellulose adsorbed by mRNA is centrifuged at 3000 rpm for 10 minutes, and the thus separated oligo(dT) cellulose is washed with 50 ml of TNE, and then with 15 ml of TNE. Subsequently, mRNA is eluted by continuous 5-times washing with 2 ml water. Determination of the absorbance shows that the total yield of mRNA is 200 μg.

Step 2 (Construction of cDNA)

400 μl of a reaction mixture containing 40 mM Tris-HCl (pH 7.5), 30 mM NaCl, 5 mM $MgCl_2$, 0.5 mM DTT (manufactured and sold by Calbiochem, U.S.A.), 20 μg/ml Oligo$(dT)_{12}$-18 (manufactured and sold by P&L Biochemicals, Inc., U.S.A.), 5 mM gGTP (manufactured and sold by Sigma Chemical Company, Inc., U.S.A.), 5 mM dCTP (manufactured and sold by Signa Chemical Company, Inc., U.S.A.), 5 mM dTTP (manufactured and sold by Sigma Chemical Company, Inc., U.S.A.), 5 mM $^{32}$P-dATP (manufactured and sold by New England Nuclear, Inc., U.S.A.), 60 μg/ml mRNA, 280 units of Avian Myeloblastosis Virus (AMV) and 600 units of reverse transcriptase (manufactured and sold by Bethesda Research Laboratories, Inc., U.S.A.) is incubated at 37° C. for one hour. Then, 0.5 M EDTA and 20% (w/v) SDS are respectively added to the reaction mixture so that the EDTA concentration and the SDS concentration become 10 mM and 0.1% (w/v), respectively. The obtained mixture is extracted with equal volume of redistilled phenol. The phenol phase is washed with a 200 μl solution containing 200 mM Tris-HCl (pH 7.5), 1 mM EDTA and 0.1% (w/v) SDS and the washings and the water phase are combined. The combined mixture is extracted with equal volume of diethyl ether and subjected to column chromatography using a column in which 3 ml of Sephadex G-100 (manufactured and sold by Pharmacia Fine Chemicals, Inc., Sweden) is packed together with TNE (hereinafter referred to as "Sephadex G-100 column"). 0.1-ml fractions are collected at a rate of 0.1 ml/min from the column. The fractions exhibiting radioactivity are combined and 3 M sodium acetate is added to the combined fractions so that the sodium acetate concentration becomes 0.3 M. Then, to the combined fractions is added ethanol in an amount of 2.5 times the volume of that of the combined fractions to precipitate nucleic acids. After cooling at −70° C. for 10 minutes, the sample is centrifuged and the supernatant is discharged. The precipitated nucleic acids are dissolved in 100 μm of distilled water. Then, 200 μl of 5 M NaOH is added to the solution. The thus obtained mixture is allowed to stand at room temperature for 40 minutes. Then, 10 μl of 5 M sodium acetate, 50 μl of distilled wter and 250 μl of ethanol are added to the mixture. After the mixture is cooled at −70° C. for 10 minutes, the resulting precipitate is centrifuged at 10,000×g at 0° C. for 20 minutes to obtain 5 μg of cDNA.

Step 3 (Construction of double stranded cDNA)

5 μg of a single stranded cDNA obtained in Step 2 is dissolved in 100 μl of $H_2O$ and heated at 100° C. for two minutes. To the obtained solution is added 250 μl of a mixture containing 0.1 M thermally denatured potassium phosphate buffer solution (pH 6.9), 10 mM $MgCl_2$, 10 mM DTT, 1 mM dATP (manufactured and sold by Schwarz Inc.), 1 mM dGTP (manufactured and sold by Schwarz Inc.), 1 mM dCTP (manufactured and sold by Schwarz Inc.), 1 mM $^3$H-dTTP (manufactured and sold by New England Nuclear Inc., U.S.A.) and [)] 150 units/ml E. coli DNA polymerase I (manufactured and sold by Boehringer Mannheim GmbH, Federal Republic of Germany). The thus obtained mixture is incubated at 15° C. for 6.5 hours. Then, 0.5 M EDTA and 20% (w/v) SDS are added to the mixture so that the EDTA concentration and SDS concentration become 10 mM and 0.1% (w/v), respectively. Then, the mixture is extracted with 250 μl of phenol (hereinafter often referred to as "phenol treatment"). The phenol phase is reextracted with 130 μl of TE buffer solution containing 20 mM Tris-HCl (pH 7.5) and 1 mM EDTA. The first water phase and the second water phase are combined together and are fractionated using a Sephadex G-100 column having a capacity of 3 ml. The fractions exhibiting radioactivity are combined and 3 M sodium acetate is added to the combined fractions so that the sodium acetate concentration becomes 0.3 M. Then, to the combined fractions is added ethanol in an amount of 2.5 times the volume of that of the combined fractions to precipitate DNA. The obtained mixture is centrifuged to obtain 7 μg of DNA. The thus obtained DNA is dissolved in 130 μl of a buffer solution containing 0.2 M NaCl, 50 mM sodium acetate (pH 4.5) and 10 mM zinc sulfate (the buffer solution is hereinafter referred to as "$S_1$ buffer solution"), followed by heating at 37° C. for 30 minutes. Then, 1.3 μl of 10 units/μl ($S_1$ buffer solution) $S_1$ nuclease is added to the obtained solution followed by incubation at 37° C. for 30 minutes. 0.5 M EDTA and 20% (w/v) SDS are added to the mixture so that the EDTA concentration and the SDS concentration become 5 mM and 0.1% (w/v), respectively. The obtained mixture is extracted with 130 μl of phenol. The phenol phase is washed with 50 μl of TE buffer solution. The water phase and the washings are combined, followed by fractionation using a Sephadex G-100 column to obtain 0.1-ml fractions. The fractions exhibiting radioactivity are collected to obtain 4 μg of double stranded cDNA.

Step 4 (Construction of dAMP-elongated DNA)

150 ng of the double stranded cDNA obtained in Step 3 is incubated at 27° C. for 8 minutes in 8 μl of dATP solution containing 1 mM dATP, 100 mM sodium cacodylate (pH 7.2), 2.5 mM $CaCl_2$, 50 μg/μl bovine serum albumin (hereinafter referred to as "BSA") and 3 to 6 units/μg (DNA) terminal deoxynucleodityl transferase (hereinafter referred to as "TdT"), followed by freezing at −70° C.

Step 5 (Cleaving of plasmid by EcoRI, Construction of dTPM-elongated pBR322)

20 μg of plasmid pBR322 and 10 units of EcoRI (manufactured and sold by Bethesda Research Laboratories, Inc., U.S.A.) are incubated at 37° C. for 2 hours in a 150 μl mixture containing 10 mM Tris-HCl (pH 7.5), 6 mM $MgCl_2$, 50 mM NaCl, 6 mM 2-mercaptoethanol and 200 μg/μl BSA. The mixture is extracted with equal volume of diethyl ether, followed by the addition of ethanol to form a precipitate. Then, the precipitate is dissolved in a 100 μl mixture containing 0.1 mM sodium glycinate (pH 9.5), 5 mM $MgCl_2$ and 50 μg/μl BSA. Into the mixture is added 17 units of λ-exonuclease, followed by incubation at 37° C. for one hour. Then, the mixture is subjected to phenol treatment, followed by the addition of ethanol to form a precipitate. The precipitate (cleaved pBR322) is added to a 300 μl reaction mixture containing 100 mM sodium cacodylate (pH 7.2), 10 mM $Na_2HPO_4$, 5 mM $MgCl_2$, 1 mM dTTP, 50 μg/μl BSA and 3–6 units/μg (DNA), TdT, followed by incubation at 37° C. for 20 minutes. Then the mixture is extracted with phenolchloform, followed by the addition of ethanol to recover plasmid.

Step 6 (Annealing of pBR322 and cDNA)

8 ng of a DNA product elongated by dAMP and 20 ng of pBR322 cleaved by EcoRI and elongated by dTMP are mixed in a 50 μl TNE buffer solution. The mixture is incubated for one hour at a temperature of each of 65° C., 45° C., 37° C. and 20° C. Then, into the mixture is added a 20 μl mixture containing 100 mM Tris-HCl (pH 7.5), 100 mM $CaCl_2$ and 100 mM $MgCl_2$, followed by cooling on ice for 20 minutes.

Step 7 (Transformation of E. coli X1776)

Colonies of E. coli X1776 strain (ATCC No. 31244) are inoculated into a 100 ml tryptone medium supplemented with 100 μg/ml diamino pimeric acid, 10 μg/ml nalidix acid and 10 μg/ml ampicillin. The E. coli X1776 strain is grown at 37° C. to an extent that the optical density of the mixture shows 0.6 to 650 nm, and then cooled on ice for 30 minutes. The culture is centrifuged at 4000 rpm for 10 minutes to precipitate cells. The cells are washed with 50 ml of 10 mM NaCl and separated by centrifugation. Then, the cells are suspended in 20 ml of 100 mM $CaCl_2$. The obtained suspension is cooled on ice for 30 minutes. After pelletting by centrifugation, the cells are resuspended in 4 ml of 100 mM $CaCl_2$ and allowed to stand on ice overnight.

The following experiments are carried out in Asahi Kasei Kogyo K.K.'s P-3 containment facility with the approval of the company's recombinant DNA security committee in accordance with the Japanese Recombinant DNA guideline.

Annealed pBR322 (recombinant DNA molecule) obtained in Step 6 in Example 3 is addedd to 100 μl of the above suspension which contains E. coli X1776 treated with $Ca^{++}$. The obtained mixture is cooled on ice for 20 minutes and kept at 20° C. for 10 minutes. Then, 0.6 ml of tryptone medium is added to the mixture. The resulting mixture is inoculated on a tryptone medium agar plate which is prepared by adding tryptone medium supplemented with 100 μg/ml diamino pimeric acid, 10 μg/ml nalidixic acid and 10 μg/ml ampicillin to an agar plate.

After the bacteria are incubated at 37° C. for 48 hours, each colony is collected and suspended in 100 μl of tryptone medium contained in each hole of a micro plate. After incubation at 37° C. overnight, 100 μl of 40% (w/v) glycerin in water is added to each hole. Then, the micro plate is kept at −20° C. There are obtained clones of each 500,000 transformants of E. coli X1776.

Step 8 (Construction of mRNA probe)

200 μg of standard SEA-induced mRNA is obtained in the same manner as described in Step 1 in Example 3. Also, 200 μg of another standard mRNA which is not induced by SEA is obtained in the same manner as described in Step 1 in Example 3 except that the procedure of inducing the SEA is not carried out. 100 μl of a solution containing 10 units of T4 polynucleotide kinase, 1mM [$_{\gamma}$-$^{32}$P]ATP, 40 mM Tris-HCl (pH 7.5), 30 mM NaCl and 5 mM $MgCl_2$ is added to 10 μg of the SEA-induced mRNA, followed by incubation at 37° C. for 10 minutes. After the kinase is inactivated by phenol treatment, 200 μg of mRNA which is not induced by SEA is dissolved into the resulting mixture. The mixture is supplemented with 3 M sodium acetate to a final concentration of 0.3 M. Then, ethanol is added to the mixture in an amount of 2.5 times the volume of that of the mixture so that 200 μg of a precipitate consisting of $^{32}$P-labelled mRNA which is induced by SEA and mRNA which is not induced by SEA are obtained. After centrifugation, the precipitate is kept at −20° C.

Step 9 (Selection of cDNA)

The transformant of E. coli X1776 obtained in Step 7 in Example 3 is inoculated into an agar plate of tryptone medium containing 10 μg/ml of ampicillin and incubated at 37° C. overnight to form colonies. Then, a circular filter having a diameter of about 82 mm is cut off from Millipore filter HAWP (manufactured and sold by Pharmacia Fine Chemicals, Inc., Sweden) and autoclaved for ten minutes. The autoclaved filter is placed on another agar plate of tryptone medium containing 10 μg/ml of ampicillin. Each of the above-obtained colonies is inoculated on the filter, followed by incubation at 37° C. overnight to form visible colonies on the filter. The filter with colonies is immersed in 0.5N NaOH for 10 minutes. The filter is immersed in 0.5 M Tris-HCl (pH 7.5) for 5 minutes. Then, the filter is immersed in a mixture containing 1.5 M NaCl and 0.5 M Tris-HCl (pH 7.5) for 5 minutes. The resulting filter is further immersed in a solution containing 0.3 M NaCl and 0.03 M sodium citrate (pH 7) [the solution is hereinafter referred to as "2×SSC (SSC=0.15 M NaCl and 0.015 M sodium citrate, pH 7) solution"] for five minutes. Then the filter is heated at 70° C. for 3 hours.

1 ml of a solution per one sheet of filter, which solution contains 50% (v/v) formamide, 4×SCC (=0.6 M NaCl and 0.006 M sodium citrate, pH 7) and 50 mM Tris-HCl (pH 7.5), is poured into a Petri dish. Then, a mRNA mixture (containing 10 μg of $^{32}$P-labelled mRNA induced by SEA and 200 μg of mRNA which is not induced by SEA) obtained in Step 8 in Example 3 is dissolved in the solution contained in the Petri dish. The above filter is impregnated with the solution and kept at 40° C. for 24 hours. Then, the filter is washed with chloroform at room temperature for 15 minutes. Such washing is repeated three times. Then, the filter is washed with a solution containing 0.6 M NaCl and 0.06 M sodium citrate (pH 7) (the solution is hereinafter referred to as "4×SCC solution") at room temperature for 15 minutes. The filter is washed with 2×SSC solution at room temperature for 15 minutes. The washing with 2×SSC solution is repeated three times. 2 ml of a 2×SSC solution containing 20 μg/ml RNase A is poured into a Petri dish. The resulting filter is placed in the Petri dish and kept at room temperature for 30 minutes. Then, the filter is washed with 2×SSC solution two times, followed by air-drying. The filter is subjected to autoradiography. Thus, it is shown that, of 500,000 colonies, 7 colonies are hybridized with the above mRNA.

Step 10 (Construction of recominant plasmid)

One of colonies obtained in Step 9 in Example 3 is inoculated into a 1-liter tryptone medium contained in a 2-liter Erlenmeyer flask, followed by shake-culture at 37° C. to an extent that the optical density of the mixture shows 0.8 at 650 nm. One liter of tryptone medium is further added to the flask. Then, chloramphenicol is added to the flask so that the chloramphenicol concentration becomes 170 μg/ml. Then, the flask is shaked at 37° C. for 16 hours. The culture is sterilized by adding 20 ml of chloroform to the flask and shaking the flask at 37° C. for 10 minutes. After the culture is separated from chloroform, the culture is centrifuged at 6000 rpm at 4° C. for 15 minutes to obtain 2 g of cells. The cells are suspended in 30 ml of 20 mM Tris-HCl (pH 7.5). After the suspension is centrifuged at 5000 rpm at 4° C. for 20 minutes, the cells are resuspended in 30 ml of 50 mM Tris-HCl (pH 7.5). A lysozyme solution containing 10 mg/ml lysozyme in 50 mM Tris-HCl (pH 7.5) is added to the obtained suspension in an amount of ¼ volume of that of the suspension. After the obtained mixture is cooled at 0° C. for 10 minutes, 0.05 M EDTA (pH 8.0) is gently added to the mixture in an amount of ¼ volume of that of the mixture without shaking. After the mixture is allowed to stand at 0° C. for 10 minutes, 2% (w/v) Triton X-100 (a surfactant manufactured and sold by Wako Junyaku Kogyo K.K., Japan) is added to the mixture in an amount of 1/16 volume of that of the mixture. After 60 minutes, the mixture is centrifuged at 10000 rpm at 0° C. for 60 minutes. The supernatant is transferrd into a beaker. Into the beaker is poured 3 M NaOH with stirring so that the solution is adjusted to pH 12.5. After stirring at 20° C. for 10 minutes, the solution is adjusted to pH 8.5. After further stirring for 3 minutes, 1/9 volume of 5 M NaCl and one volume of phenol are added to the solution and vigorously stirred for 5 minutes, followed by centrifugation at 10000 rpm at 0° C. for 10 minutes to be phase-separated. The supernatant containing circular double stranded DNA is carefully separated from the medium phase containing a single stranded DNA. The supernatant is extracted with chloroform three times. 5 mg/ml pancreatic RNase A is added to the extract containing a circular double stranded DNA so that the pancreatic RNAse A concentration becomes 20 μg/ml. The obtained mixture is incubated at 37° C. for 60 minutes. 5 m NaCl is added to the mixture in an amount of 1/5 volume of that of the mixture. Then, the mixture is supplemented with 30% (w/v) Polyethylene Glycol 6000 (manufactured and sold by Union Carbide Corporation, U.S.A.) in water which is sterilized prior to use to a final concentration of 7.5% (w/v). After the obtained mixture is kept at −10° C. for 14 hours, the mixture is centrifuged at 8000 rpm at 0° C. for 20 minutes to collect a precipitate. The precipitate is dissolved in a solution containing 0.075 M NaCl and 0.0075 M sodium citrate so that the optical density of the solution shows 20 at 260 nm. Then, 20% (w/v) SDS is added to the obtained solution so that the SDS concentration becomes 0.5% (w/v). The solution is supplemented with pronase so that the pronase concentration becomes 0.5 mg/ml, and incubated at 37° C., for 30 minutes. The solution is extracted with equal volumes of phenol three times and with equal volumes of chloroform two times. The obtained plasmids are subjected to sucrose gradient sedimentation at 20000 rpm at 15° C. for 15 hours in Beckmann SW-27 rotor so that fractionation is attained. In centrifuging, a solution containing 50 mM Tris-HCl (pH 7.5) and 1 mM EDTA and having a sucrose gradient, 5 to 23% (w/v), is used. The optical density of each of the obtained fractions is determined at 260 nm. The fractions containing DNA are collected, and the DNA is precipitated using sodium acetate and ethanol in the same manner as mentioned above. After centrifugation, 50 μg of circular double stranded DNA is obtained.

Step 11 (Cleavage of Plasmid)

20 μg of the circular double stranded DNA obtained in Step 10 in Example 3 is incubated at 37° C. for 2 hours in a 150 μl mixture containing 10 mM Tris-HCl (pH 7.5), 6 mM $MgCl_2$, 50 mM NaCl, 6 mM 2-mercaptoethanol, 200 μg/μl BSA and 20 units of restriction enzyme EcoRI. Then, pronase, EDTA and SDS are added to the mixture so that the pronase concentration. the EDTA concentration and the SDS concentration become 0.5 mg/ml, 10 mM and 0.5% (w/v), respectively. After the obtained mixture is kept at 37° C. for 30 minutes, the mixture is extracted with 30 μl of phenol-chloroform (1:1 by volume). The non-aqueous phase is washed with a 50 μl solution containing 20 mM Tris-HCl (pH 7.5) and 1 mM EDTA. The washings and the aqueous phase are combined, followed by three-time extraction with diethyl ether. To the combined aqueous solution is added 1/10 volume of 3 M sodium acetate and 2.5 times volume of ethanol to form a precipitate again. Then, the mixture is cooled at −70° C. for 5 minutes, followed by centrifugation to obtain 9 μg of DNA.

Step 12 (Cleavage by restriction PstI)

Substantially the same procedures as described in Step 11 in Example 3 are repeated except that 5 μg of plasmid cleaved with EcoRI which is obtained in Step 11 in Example 3 is used instead of 20 μg of the circular double stranded DNA and that a restriction enzyme PstI is used instead of the restriction enzyme EcoRI to obtain a PstI-cleaved DNA-fragment mixture. The mixture is separated by electrophoresis in a 2% (w/w) flat agarose gel (10×20×0.7 cm) in which 50 mM Tris-acetic acid buffer solution (pH 7.8) is contained so that about 0.2 μg of a PstI-cleaved DNA is obtained.

Step 13 (Partial cleavage by restriction enzyme BstNI)

0.2 μg of the PstI-cleaved DNA obtained in Step 12 is incubated at 37° C. for 5 minutes in a 150 μl solution containing 10 mM Tris-HCl (pH 7.5), 6 mM $MgCl_2$, 50 mM NaCl, 6 mM 2-mercaptoethanol, 200 μg/μl BSA and two units of a restriction enzyme BstNI to cleave the DNA partially. Then, phenochloroform treatment, ethanol treatment and electrophoresis treatment are carried out in accordance with the procedures described in Step 11 in Example 3 to obtain 10 ng of BstNI-partially cleaved DNA fragments. Subsequently, oligodeoxynucleotides prepared in the same manner as mentioned in Steps 1 to 5 in Example 2, of which the formulae are as follows:

AATTCATGTGTATC

GTCCTAGGCTCCCTC

GGCTGTTATTGTC

TGACAATA

ACAGCCGAGGGAGCC

TAGGACGATACACATG (wherein A, G, C and T are as defined before and wherein the left end of each formula and the right end of each formula represent 5'-hydroxyl group side and 3'-hydroxyl group side, respectively), and the above partially cleaved DNA fragments are annealed one another and ligated, by means of a T4 DNA ligase, in the same manner as mentioned in Step 6 in Example 2.

Step 14 (Expression of peptides in E. coli)

In accordance with the method described in David V. Goeddel et al, Nature, 287, 411 (1980), the above obtained DNA is inserted into the sheared portion of pBR322, which portion is formed by shearing action of EcoRI and PstI; EcoRI-cleaved fragments consisting of 300 base pairs and including a promoter of tryptophan of E. coli, an operator of tryptophan of E. coli and a ribsome binding site are constructed; and the fragments are bound to the above pBR322 containing the intended DNA. The obtained plasmid is contacted with E. coli X1776 strain so that the E. coli X1776 strain is transformed. From the cultures obtained by incubation of the transformed strain, a peptide is separated by using a monoclonal antibody which specifically bonds to the peptide (HC(0), which antibody is obtained in accordance with the method described in David. S. Secher et al, Nature, 285, 446 (1980) by using the peptide HC(0) obtained in Example 1 as an antigen. The obtained peptide is subjected to amino acid sequence analysis. As a result of this, the amino acid sequence of the obtained peptide is in agreement with that of peptide MC(0).

EXAMPLE 4

The following experiment is performed in a manner similar to that as shown by D. V. Goeddel at the 2nd Annual International Congress for Interferon Research. The Hind III-Pvu II fragment encompassing the SV40 replication origin [see R. M. Myers et al, Proc. Natl. Acad. Sci. U.S.A., 77, 6491 (1980)] is converted to a fragment bounded by EcoRI restriction sites. The Hind III site is converted to an EcoRI site by addition of synthetic oligomer and the Pvu II site is converted by ligation to an EcoRI site which has been filled-in using DNA polymerase I (Klenow fragment). The EcoRI fragment containing the SV 40 origin is ligated into the EcoRI site of pML-1 [see M. Lusky et al, Nature, 293, 79 (1981)]. The resulting expression vector is chosen which contained the SV 40 late promoter oriented to read away from the ampicillin resistance gene of pML-1. The Eco RI site nearest the ampicillin resistance gene is destroyed by partial EcoRI digestion, filling in with the Klenow fragment of DNA polymerase I, and subsequent ligation [see K. Itakura et al, Science, 198, 1056 (1977)]. The PstI insert of the plasmid obtained in Example 2 is converted to a fragment bounded by EcoRI sites by insertion in the PstI site. The EcoRI-flanked cDNA insert is ligated into the single EcoRI site of the pML-SV 40 expression vector to give the plasmid PTI-SV40. This vector is introduced by a transfection into the transformed monkey cell line COS-7 [see Y. Gluzman, Cell, 23, 175 (1981)]. COS-7 endogeneously expresses SV-40 large T antigen and has been shown to permit the propagation of recombinant plasmids containing pML-1 and SV40 origin sequences. Cell media from transfected culture are assayed daily for the presence of interferon as shown in Example 2. Yield of 100 units per ml is obtained 3 or 4 days after transfection, indicating that the interferon is being secreted into the culture medium by the COS-7 cells.

EXAMPLE 5

The following experiment is performed in a manner similar to that as described in R. A. Hitzeman et al, Nature, 293, 717 (1981). Ten μg of XhoI-cut pACF301 is incubated with 0.2 unit of Bal 31 nuclease (BRL) for 15 sec at 30° C. in an aqueous mixture of 20 mM Tris-HCl (pH 8.1), 12 mM $CaCl_2$, 12 mM $MgCl_2$, 0.2 MNaCl, 1mM EDTA and 0.1 μg/μl bovine serum albumin (BSA). During the time, about 50 base pairs of the DNA are removed. A 1 μg aliquot of this DNA is incubated with DNA polymerase I (Klenow fragment) and deoxynribonucleoside triphosphate to fill in the ends, and then incubated with T4 DNA ligase and synthetic EcoRI linker (manufactured and sold by Collaborative Research, U.S.A.) for 12 hours at 14° C. The DNA is then cleaved with EcoRI and BamHI restriction nuclease, and the mixture of fragments containing variously deleted ADH1 promoter sequences is isolated by preparative electrophoresis on 1% by weight aqueous agarose gel. The mixture of electro-eluted fragment is ligated with the large EcoRI-BamHI fragment of pBR322, and the individual clones are selected by transformation of E. coli strain RRI (ATCC 31343), selecting for the ampicillin resistance colonies. DNA from individual colonies is prepared by a quick-screening procedure [see H.C. Birnboim et al, Nucleic Acids Res., 7, 1513 (1979)]. The length of each deletion is estimated by cleaving each plasmid with EcoRI endonuclease, 3'-end labelling with Klenow polymerase plus [$\alpha$-$^{32}$P]dATP, then cleaving the DNA with endonuclease AluI and sizing the resulting small fragments on a urea-acrylamide gel.

pFRL4 is constructed from YRp7 [see G. Tschumper et al, Gene, 10, 157 (1980)] by removing both EcoRI sites (Klenow DNA polymerase I fill-in of sticky ends, followed by blunt-end ligation) and replacement of one EcoRI site using the small Hind III fragment of YRp7 to replace the small HindIII fragment of the plasmid lacking both EcoRI sites. Twenty μg of pFRL4 is digested with BamHI and EcoRI, then electrophoresed on 1% by weight agarose gel. The large (5000 base pairs) fragment is cut from the gel, electro-eluted extracted twice with phenol and chloroform before ethanol precipitation. Three μg of this fragment is then separately ligated with 1 μg of the promoter-containing fragments for 12 hours at 15° C. in 50 μl of an aqueous mixture of 20 mM Tris-HCl (pH 7.5), 10 mM $MgCl_2$, 10 mM dithiothreitol, and 0.5 mM ATP, containing 0.5 unit of T4 DNA ligase. E. coli K-12 strain 294 (ATCC 31446) is transformed with the ligation mix to ampicillin resistance, and plasmids from transformation mixtures are purified. Fifty μg of the plasmid obtained in Example 2 is digested with EcoRI, then electrophoresed on a 1.2% by weight aqueous agarose gel. The DNA fragment coding the peptide is cut from the gel, electro-eluted and extracted twice with phenol-chloroform before ethanol precipitation. The DNA fragment coding the peptide is ligated into the unique EcoRI site in the pFRP plasmid which have been previously cut with EcoRI and treated with bacterial alkaline phosphatase. The plasmid is then analysed by Bgl II restriction analysis and used for yeast transformations. Recombinant plasmids, in which DNA coding the peptide is placed either in parallel or antiparallel orientation between each of the ADH promoter fragments for the TRPI gene, are introduced into yeast, using standard transformation procedures [see A. Hinnen et al, Proc. Natl. Acad. Sci., U.S.A., 75, 1929 (1978)]. Spheroplasts of yeast recipient strain RH218 (Trp1) (ATCC 44076) [are] separately incubated with the DNA of the plasmid, and the mixture is then placed in agar without tryptophan to select transformant colonies. Cultures of each transformant are grown using selective pressure in liquid medium without tryptophan, collected in mid-log phase and used to prepare cell extracts by spheroplasting and guanidine hydrochloride lysis. A substantial level of bioactivity is observed in all transformants with plasmids having the DNA coding the peptide in the correct orientation.

What is claimed is:

[1. A physiologically active peptide represented by the following formula (I):

$$BCysX_1CysX_2CysX_3 \quad (I)$$

wherein B stands for a hydrogen atom or a methionyl group, Cys a cysteine residue, $X_1$ 5 to 9 amino acid residues, $X_2$ one amino acid residue, and $X_3$ 138 to 148 amino acid residues.]

[2. A peptide according to claim 1, wherein $X_1$ stands for 7 amino acid residues and $X_3$ stands for 143 amino acid residues.]

[3. A peptide according to any of claims 1 or 2, wherein $X_1$ stands for an isoleucylvalylleucylglyclseryl-leucylglycine residue and $X_2$ stands for a tyrosine residue.]

4. A *physiologically active* peptide [according to claim 1,] *represented by the formula (I):*

$$BCysX_1CysX_2CysX_3 \quad (I)$$

wherein *B stands for a hydrogen atom or a methionyl group, Cys stands for a cysteine residue,* $X_1$ stands for an isoleucylvalylleucylglycylserylleucylglycine residue, $X_2$ stands for a tyrosine residue and $X_3$ stands for a residue *of amino acid sequence* represented by the following formula (II):

[Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn

2. Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln] *Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln* wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue. Asn an aspargine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Met a methionine residue.

*5. A peptide comprising an amino acid sequence represented by the following formula (II): Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln*

*wherein Gln stands for a glutamine residue, Asp as aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Met a methionine residue.*

* * * * *

UNITED STATES PATENT AND TRADEMARK OFFICE

CERTIFICATE OF CORRECTION

PATENT NO. : Re. 32,637

DATED : April 5, 1988

INVENTOR(S) : TORAO ISHIDA

It is certified that error appears in the above-identified patent and that said Letters Patent is hereby corrected as shown below:

Col. 1, line 21, change "isoleucylvalleucylglycylserylleucylglyceine" to --isoleucylvalylleucylglycylserylleucylglycine--.

Col. 2, line 20, delete "5 to 9 aminoacid resi".

line 21, delete entire line.

line 22, delete entire line.

line 23, delete "due, X, [5 to 9 amino acid residues]".

Col. 4, line 9, change "as" to -- an--.

line 10, change "glycerine" to --glycine--.

Col. 5, line 47, change "w/v" to --(w/v)--.

line 51, change "$\gamma$- amino" to -- $\alpha$ -amino--.

Col. 10, line 56, change "Boc-valine a valine" to --Boc-valine: a valine--.

UNITED STATES PATENT AND TRADEMARK OFFICE

CERTIFICATE OF CORRECTION

PATENT NO. : Re. 32,637

DATED : April 5, 1988

INVENTOR(S) : TORAO ISHIDA

It is certified that error appears in the above-identified patent and that said Letters Patent is hereby corrected as shown below:

Col. 12, line 31, change "stirred" (first occurrence) to --added--.

Col. 13, line 59, change "$Na_2SP_4$" to --$Na_2SO_4$--.

Col. 24, line 48, change $Na_2PO_2.2H_2O$" to --$Na_2HPO_4.2H_2O$--.

Col. 25, line 45, change "gGTP" to --dGTP--.

Col. 26, line 16, change "wter" to --water--.

Col. 27, line 15, change "dTPM" to --dTMP--.

Col. 27, line 53, change "nalidix" acid to --nalidixic acid--.

Col. 28, line 27, change "inducing the SEA" to --inducing by SEA--.

Col. 29, line 46, change "0.05" to --0.5--.

line 68, change "RNAse" to --RNase--.

UNITED STATES PATENT AND TRADEMARK OFFICE

CERTIFICATE OF CORRECTION

PATENT NO. : Re. 32,637

DATED : April 5, 1988

INVENTOR(S) : TORAO ISHIDA

It is certified that error appears in the above-identified patent and that said Letters Patent is hereby corrected as shown below:

Col. 33, line 29, after "(ATCC 44076)", insert --[See G. Miozarri et al., Journal of Bacteriology, 134, 48-59 (1978)]--.

Col. 33, line 54, change "isoleucylvalylleucylglyclserylleucylglycine" to --isoleucylvalylleucylglycylserylleucylglycine--.

Signed and Sealed this

Fifteenth Day of November, 1988

*Attest:*

*Attesting Officer*

DONALD J. QUIGG

*Commissioner of Patents and Trademarks*